United States Patent
Desai et al.

(10) Patent No.: US 10,743,859 B2
(45) Date of Patent: Aug. 18, 2020

(54) SURGICAL END EFFECTORS

(71) Applicant: Covidien LP, Mansfield, MA (US)

(72) Inventors: Arpan Desai, Hamden, CT (US); Paul C. DiCesare, Easton, CT (US); Danial Ferreira, Woodbridge, CT (US); Brandon Michael Zalewski, Plymouth, CT (US)

(73) Assignee: COVIDIEN LP, Mansfield, MA (US)

( * ) Notice: Subject to any disclaimer, the term of this patent is extended or adjusted under 35 U.S.C. 154(b) by 313 days.

(21) Appl. No.: 15/678,149

(22) Filed: Aug. 16, 2017

(65) Prior Publication Data

US 2018/0110509 A1    Apr. 26, 2018

Related U.S. Application Data

(60) Provisional application No. 62/410,876, filed on Oct. 21, 2016.

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0401* (2013.01); *A61B 17/062* (2013.01);
(Continued)

(58) Field of Classification Search
CPC ............ A61B 17/0401; A61B 17/0469; A61B 17/06004; A61B 17/06066;
(Continued)

(56) References Cited

U.S. PATENT DOCUMENTS 3,596,528 A    8/1971 Dittrich et al.
3,866,510 A    2/1975 Eibes et al.
(Continued)

FOREIGN PATENT DOCUMENTS

EP    0374088 A1    6/1990
JP    S60129041 A    7/1985
(Continued)

OTHER PUBLICATIONS

Partial European Search Report corresponding to counterpart European Patent Appln. No. EP 17 19 7448.8 dated Jan. 12, 2018.
(Continued)

*Primary Examiner* — George J Ulsh

(57) ABSTRACT

According to an aspect of the present disclosure, an end effector for use with a surgical device is provided. The end effector includes a drive assembly, a driver, a needle assembly and a biasing element. The driver is disposed in mechanical cooperation with the drive assembly. Rotation of the drive assembly in a first direction causes distal translation of the driver with respect to the drive assembly. The needle assembly is disposed in mechanical cooperation with the driver. Distal translation of the driver causes a corresponding distal translation of the needle assembly. The biasing element is disposed in mechanical cooperation with the needle assembly and is configured to bias the needle assembly proximally.

16 Claims, 35 Drawing Sheets

(51) Int. Cl.
*A61B 17/06* (2006.01)
*A61B 17/34* (2006.01)
*A61B 17/00* (2006.01)
*A61B 17/29* (2006.01)

(52) U.S. Cl.
CPC .. *A61B 17/06004* (2013.01); *A61B 17/06066* (2013.01); *A61B 17/06166* (2013.01); *A61B 17/0493* (2013.01); *A61B 2017/003* (2013.01); *A61B 2017/00367* (2013.01); *A61B 2017/00473* (2013.01); *A61B 2017/0409* (2013.01); *A61B 2017/0417* (2013.01); *A61B 2017/0427* (2013.01); *A61B 2017/0458* (2013.01); *A61B 2017/0464* (2013.01); *A61B 2017/0472* (2013.01); *A61B 2017/061* (2013.01); *A61B 2017/06019* (2013.01); *A61B 2017/06023* (2013.01); *A61B 2017/06042* (2013.01); *A61B 2017/06052* (2013.01); *A61B 2017/06176* (2013.01); *A61B 2017/2903* (2013.01); *A61B 2017/3409* (2013.01)

(58) Field of Classification Search
CPC ............ A61B 17/06166; A61B 17/062; A61B 2017/003; A61B 2017/00367; A61B 2017/00473; A61B 2017/0409; A61B 2017/0417; A61B 2017/0427; A61B 2017/0458; A61B 2017/0464; A61B 17/0493; A61B 2017/06019; A61B 2017/06023; A61B 2017/06042; A61B 2017/06052; A61B 2017/061; A61B 2017/06176; A61B 2017/2903; A61B 2017/3409
See application file for complete search history.

(56) References Cited

U.S. PATENT DOCUMENTS

| | | |
|---|---|---|
| 4,350,491 A | 9/1982 | Steuer |
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross |
| 5,246,450 A | 9/1993 | Thornton et al. |
| 5,249,583 A | 10/1993 | Mallaby |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,702,420 A | 12/1997 | Sterling et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,402,780 B1 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |

(56) References Cited

U.S. PATENT DOCUMENTS

| | | |
|---|---|---|
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |
| 7,740,159 B2 | 6/2010 | Shelton, IV et al. |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,181,840 B2 | 5/2012 | Milliman |
| 8,216,254 B2 | 7/2012 | McLean et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,783,329 B2 | 10/2017 | Sniffin et al. |
| 9,788,833 B2 | 10/2017 | Zergiebel et al. |
| 2003/0009441 A1 | 1/2003 | Holsten et al. |
| 2004/0015177 A1 | 1/2004 | Chu |
| 2004/0092937 A1 | 5/2004 | Criscuolo et al. |
| 2005/0222665 A1 | 10/2005 | Aranyi |
| 2006/0129152 A1 | 6/2006 | Shipp |
| 2007/0038220 A1 | 2/2007 | Shipp |
| 2007/0088390 A1 | 4/2007 | Paz et al. |
| 2007/0106317 A1 | 5/2007 | Shelton et al. |
| 2007/0162030 A1 | 7/2007 | Aranyi et al. |
| 2008/0097523 A1 | 4/2008 | Bolduc et al. |
| 2008/0312687 A1 | 12/2008 | Blier |
| 2009/0112234 A1 | 4/2009 | Crainich et al. |
| 2009/0118776 A1 | 5/2009 | Kelsch et al. |
| 2009/0131872 A1 | 5/2009 | Popov |
| 2009/0216154 A1 | 8/2009 | Lin Lee |
| 2010/0270354 A1 | 10/2010 | Rimer et al. |
| 2011/0022065 A1 | 1/2011 | Shipp |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2012/0323261 A1 | 12/2012 | Gaynor et al. |
| 2013/0116709 A1 | 5/2013 | Ziniti et al. |
| 2014/0005678 A1 | 1/2014 | Shelton, IV et al. |

(56) References Cited

U.S. PATENT DOCUMENTS

| | | |
|---|---|---|
| 2014/0014707 A1 | 1/2014 | Onukuri et al. |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2015/0032130 A1 | 1/2015 | Russo |
| 2015/0133970 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0045222 A1 | 2/2016 | Lee |
| 2016/0074034 A1 | 3/2016 | Shipp |
| 2016/0166255 A1 | 6/2016 | Fischvogt |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0302824 A1* | 10/2016 | Sato ................. A61B 1/00 |
| 2016/0338694 A1 | 11/2016 | Kayan |
| 2016/0345967 A1 | 12/2016 | Sniffin et al. |

FOREIGN PATENT DOCUMENTS

| | | |
|---|---|---|
| JP | 09149906 | 6/2014 |
| WO | 93/16644 A1 | 9/1993 |
| WO | 03/037194 A1 | 5/2003 |

OTHER PUBLICATIONS

Extended European Search Report corresponding to counterpart Patent Appln. EP 17 19 7477.7 dated Jul. 23, 2018.
Extended European Search Report corresponding to counterpart EP Appln. No. 17 19 7448.8 dated May 15, 2018.
Extended European Search Report corresponding to EP 14 15 8946.5, completed Jun. 20, 2014 and dated Jul. 8, 2014; (9 pp).
Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
EP Search Report corresponding to EP 14 18 1900.3, completed Mar. 31, 2015 and dated Apr. 9, 2015; 7pp.
Extended European Search Report corresponding to counterpart application EP 14 19 7885.8 dated Apr. 30, 2015; 9pp.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
European Search Report corresponding to EP No. 10 01 2659.8, completed Dec. 21, 2010; dated Jan. 3, 2011; 3 pages.
European Search Report corresponding to EP No. 10 01 2646.5, completed Feb. 11, 2011; dated Feb. 22, 2011; 3 pages.
Extended European Search Report corresponding to Int'l Application No. EP 14 15 1663.3 dated Jun. 7, 2016.
Supplementary European Search Report dated Feb. 2, 2017 in corresponding European Patent Application No. 14817036, 8 pages.
European Search Report dated May 10, 2017 in corresponding European Patent Application No. 17157259.7, 12 pages.
Extended European Search Report corresponding to counterpart European Patent Appln. No. EP 17 19 7455.3 dated Jan. 17, 2018.

* cited by examiner

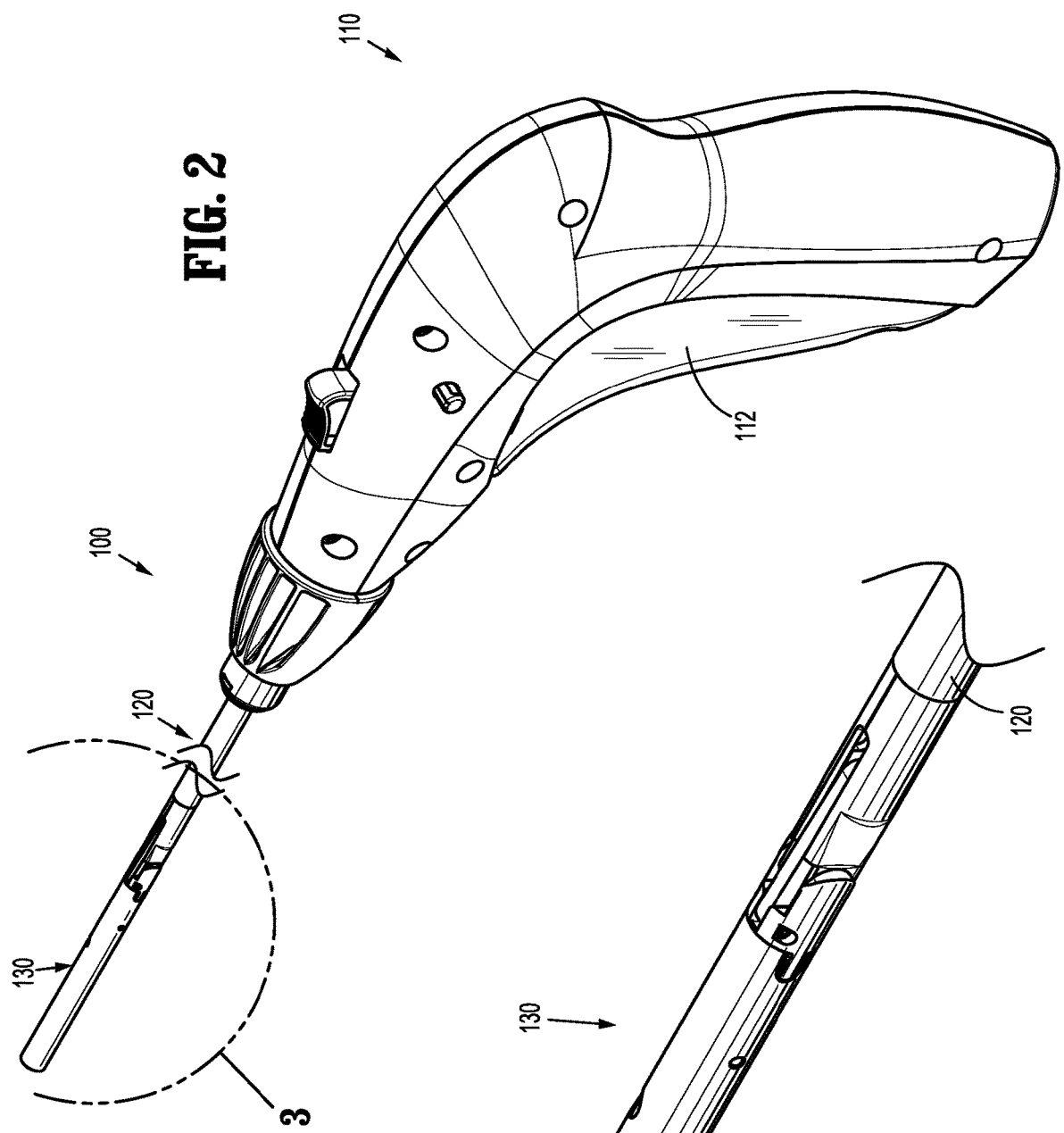

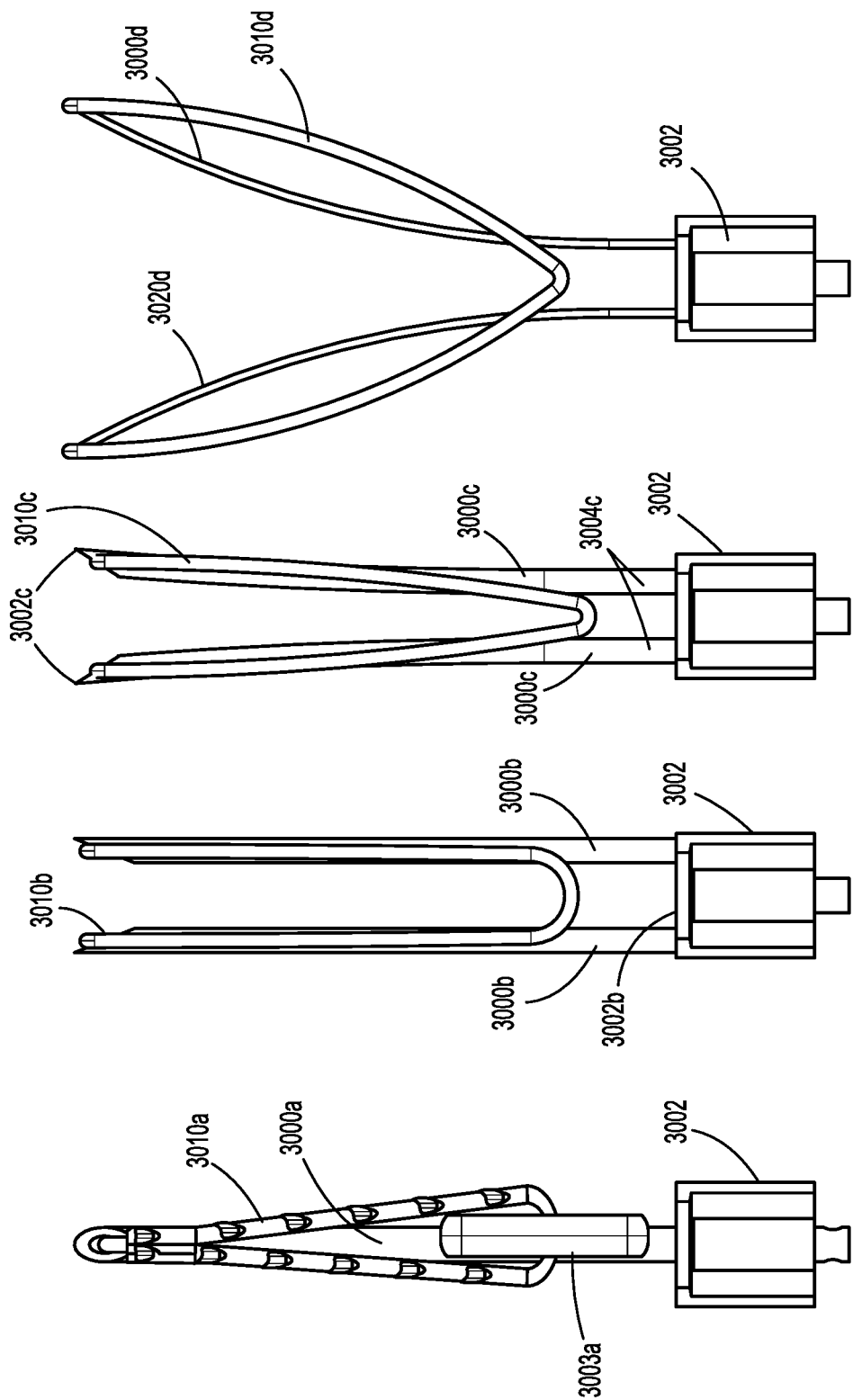

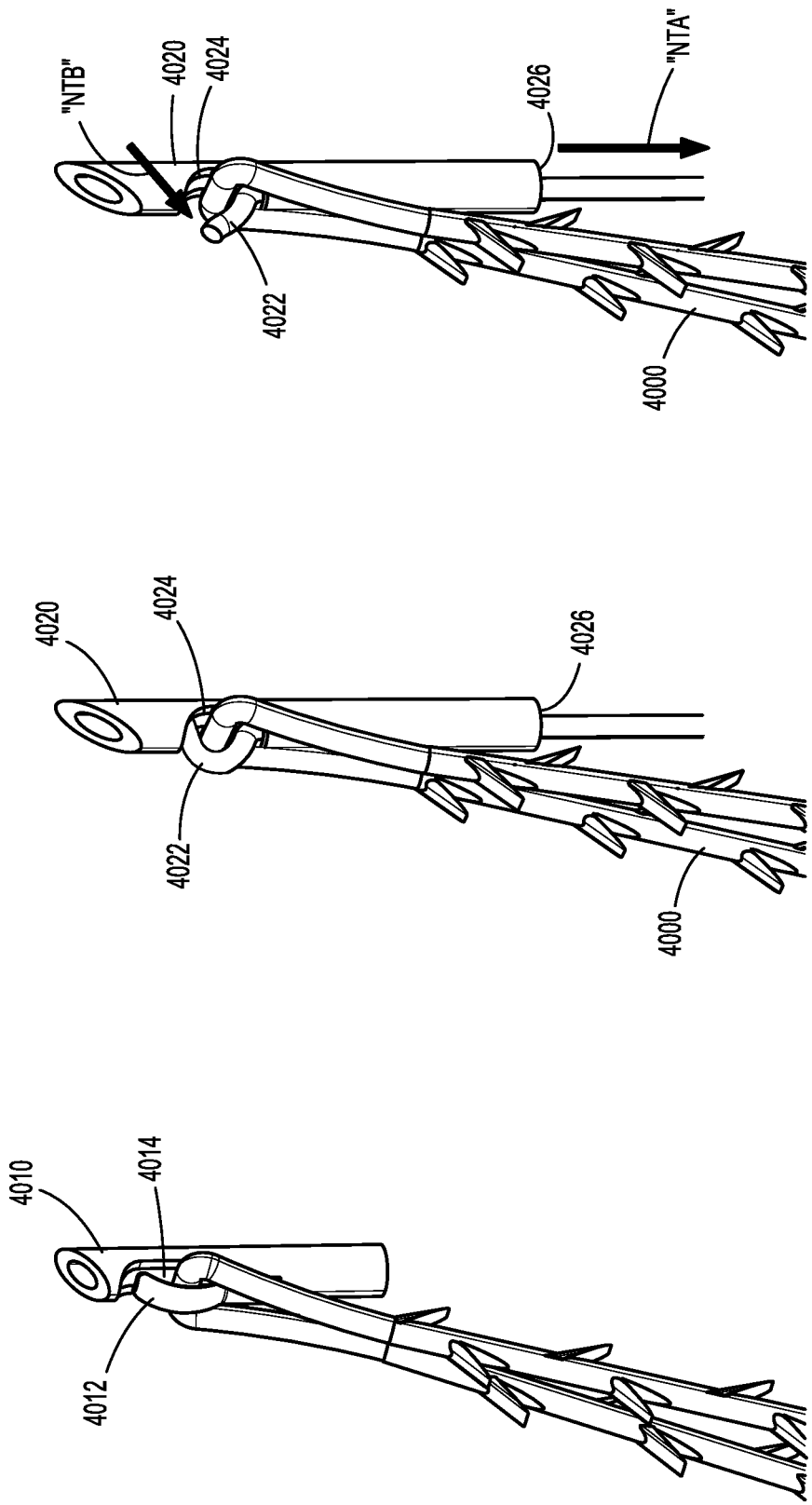

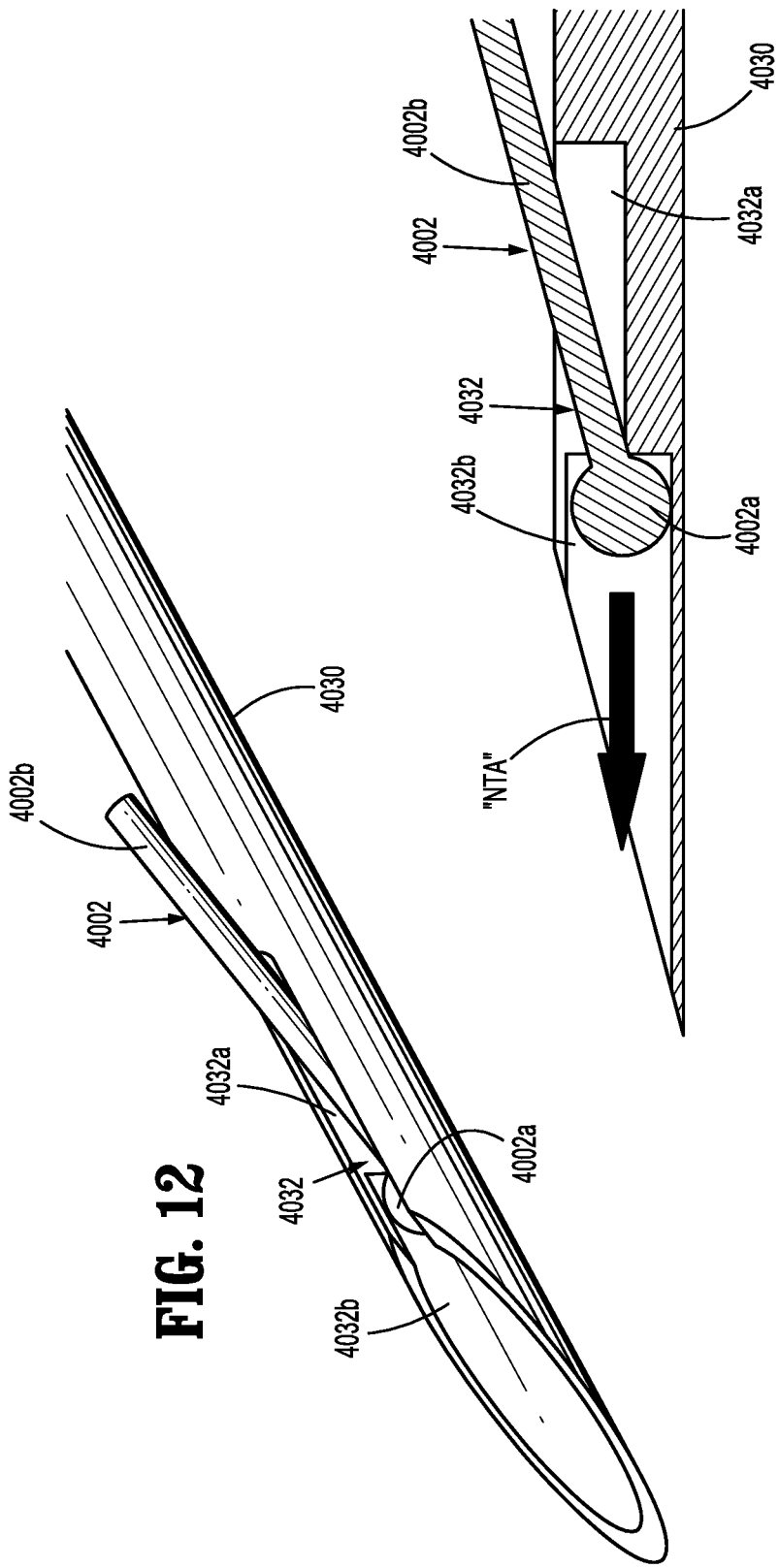

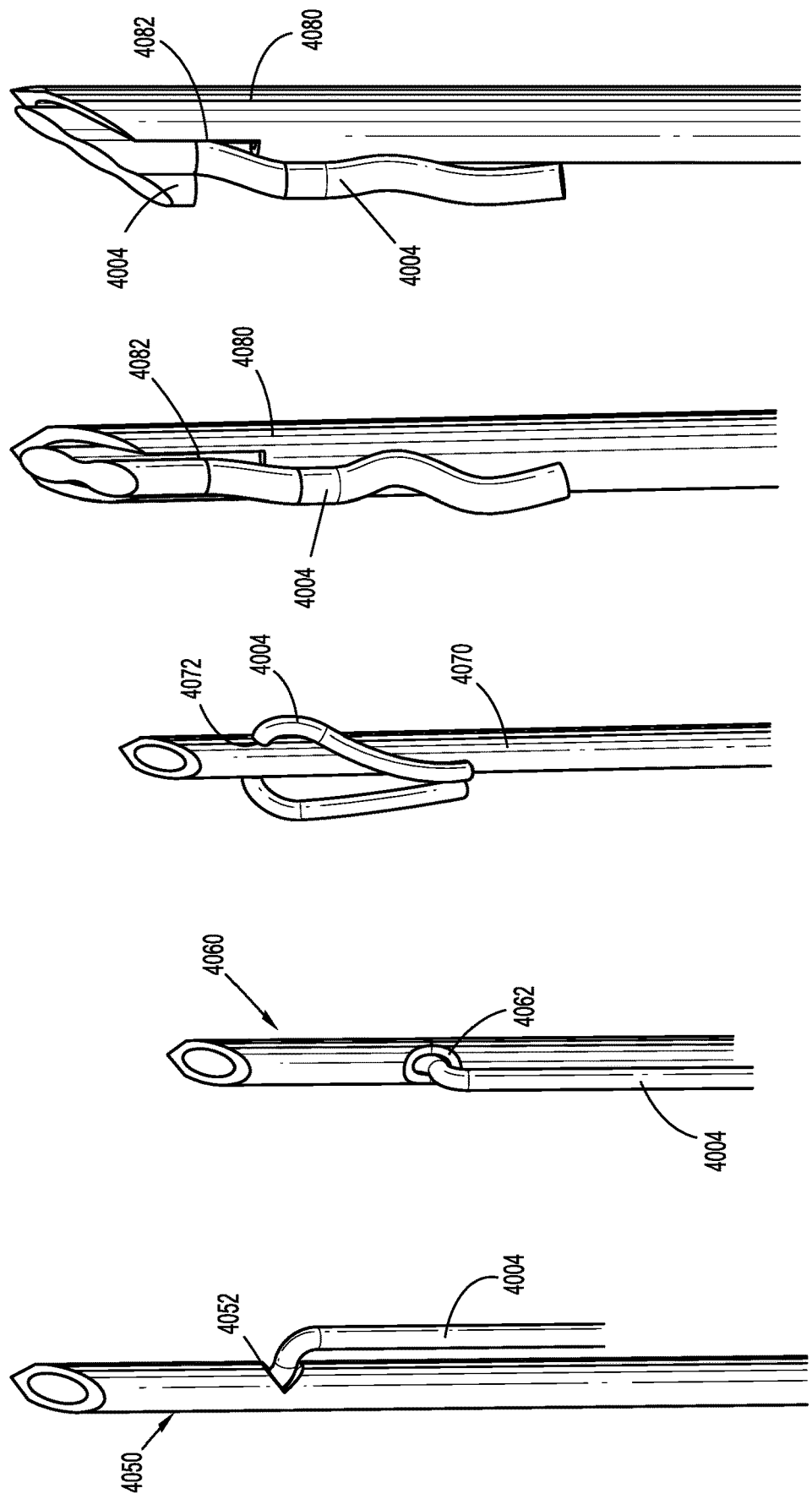

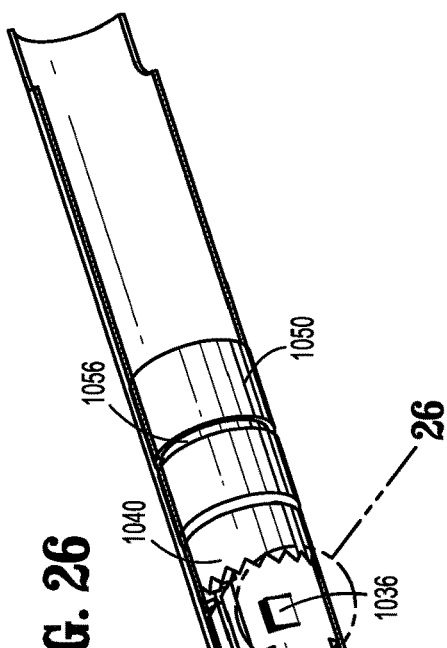
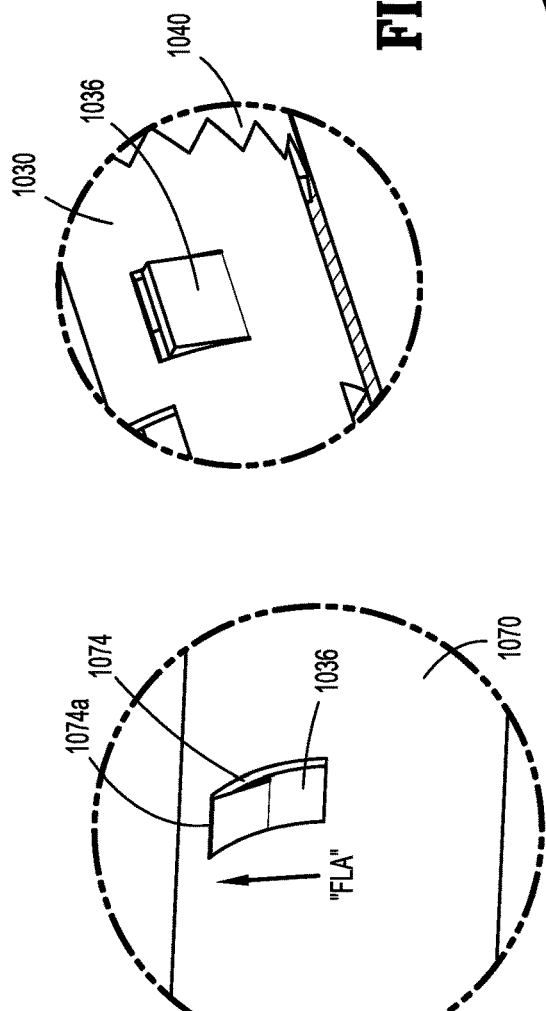
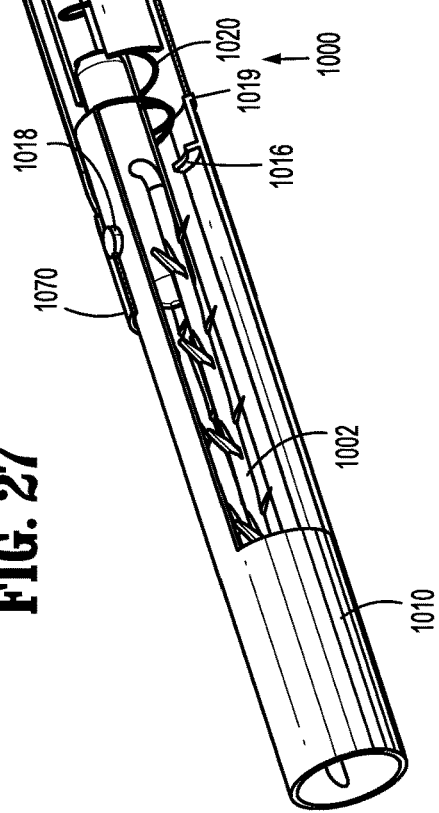

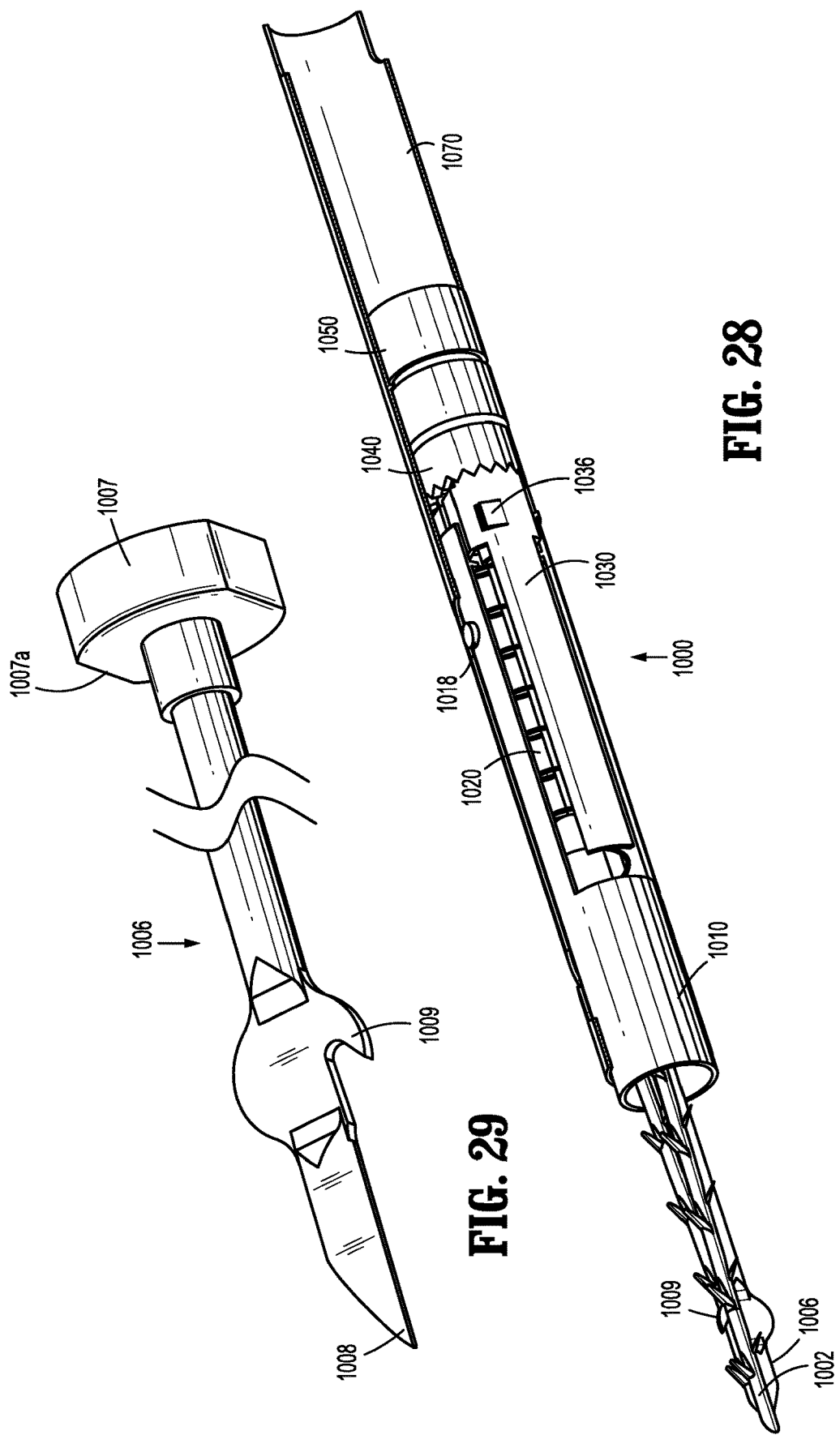

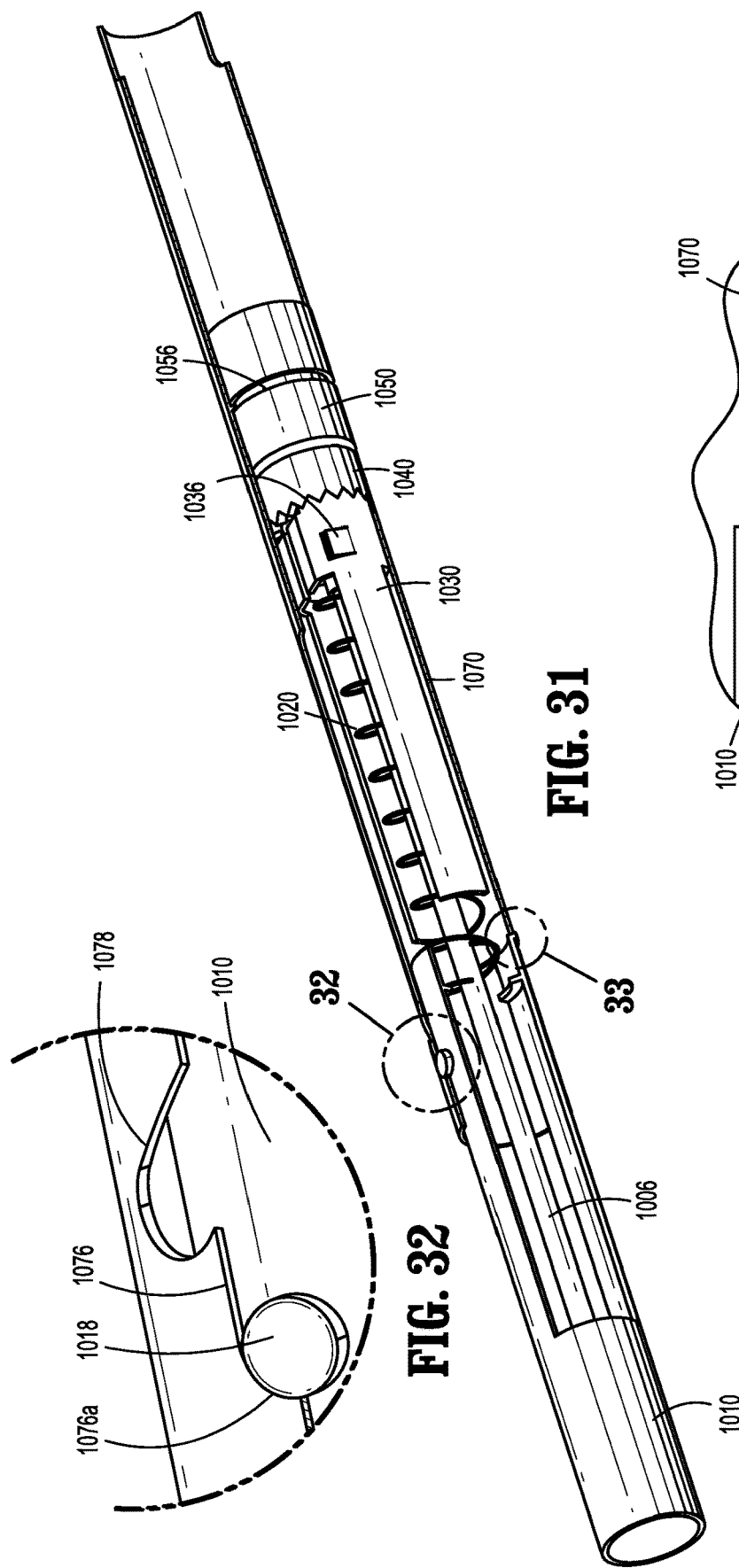
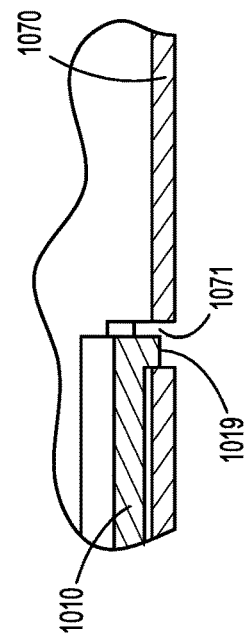
FIG. 31
FIG. 32
FIG. 33

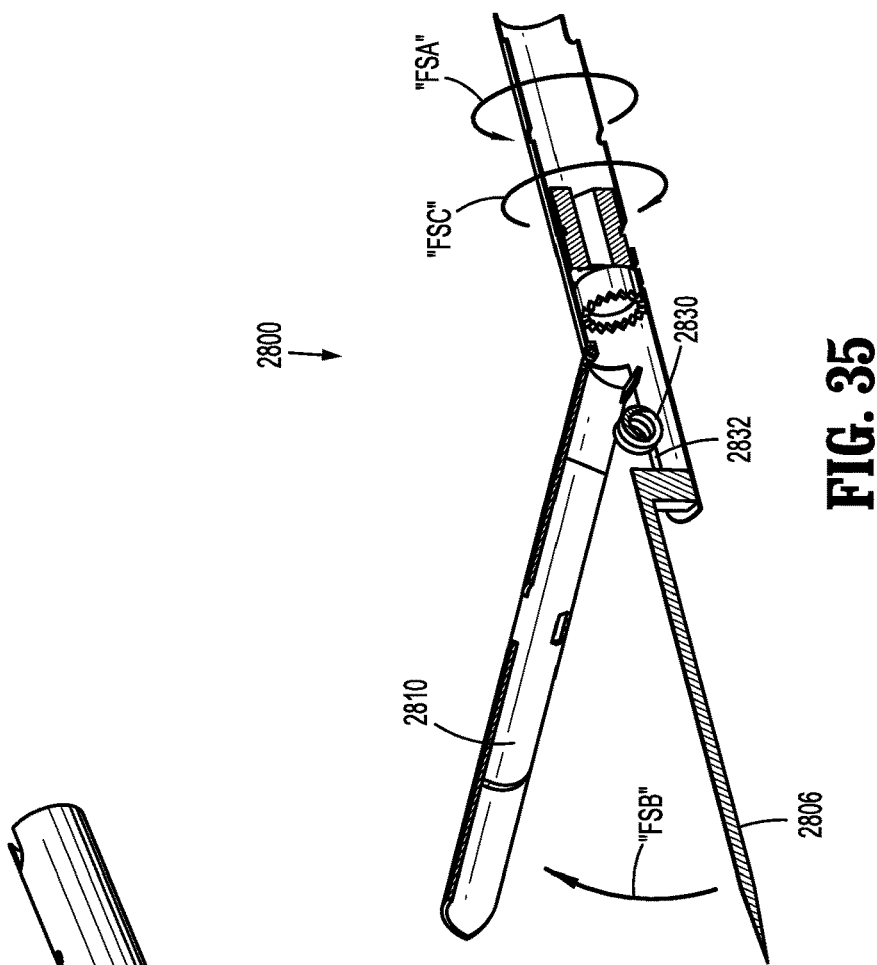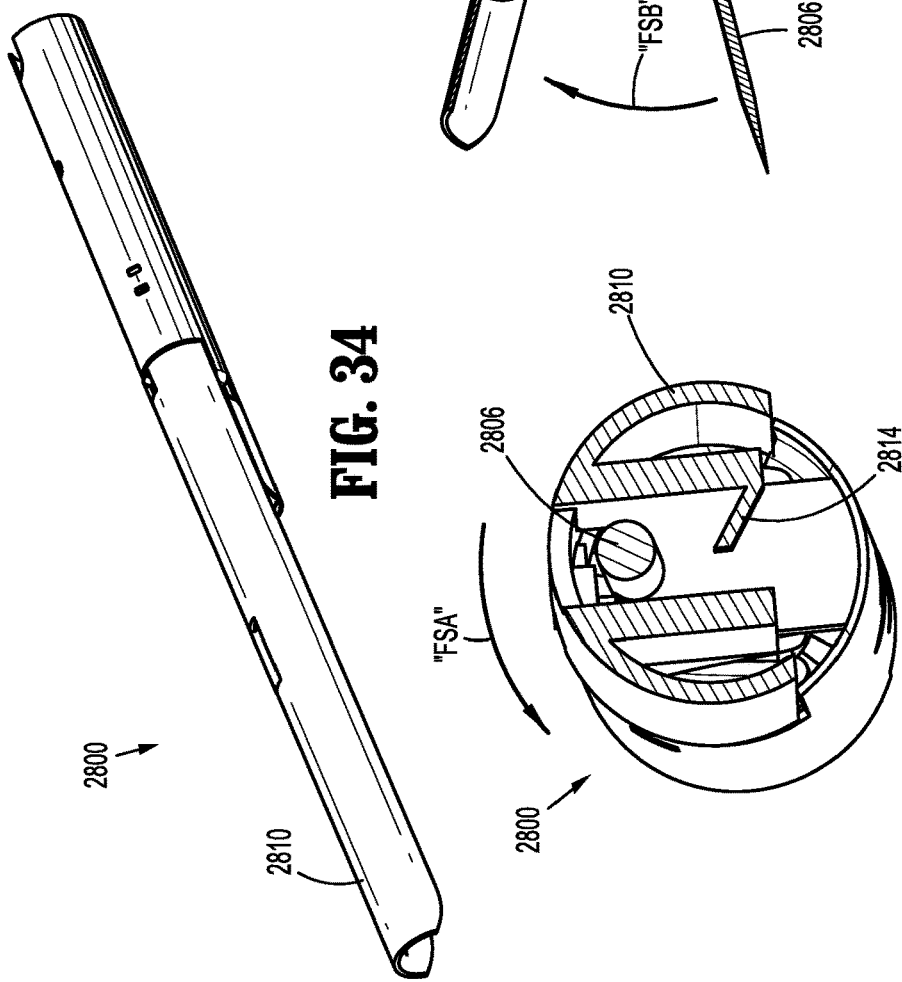

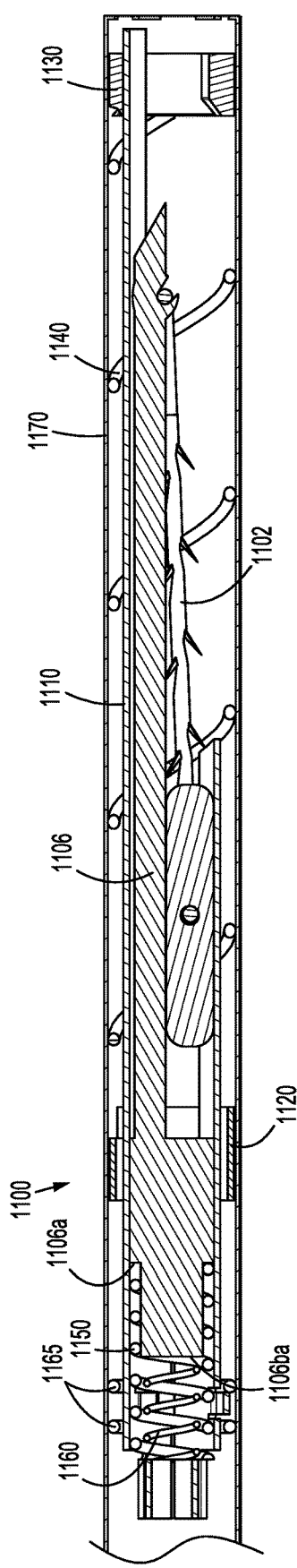
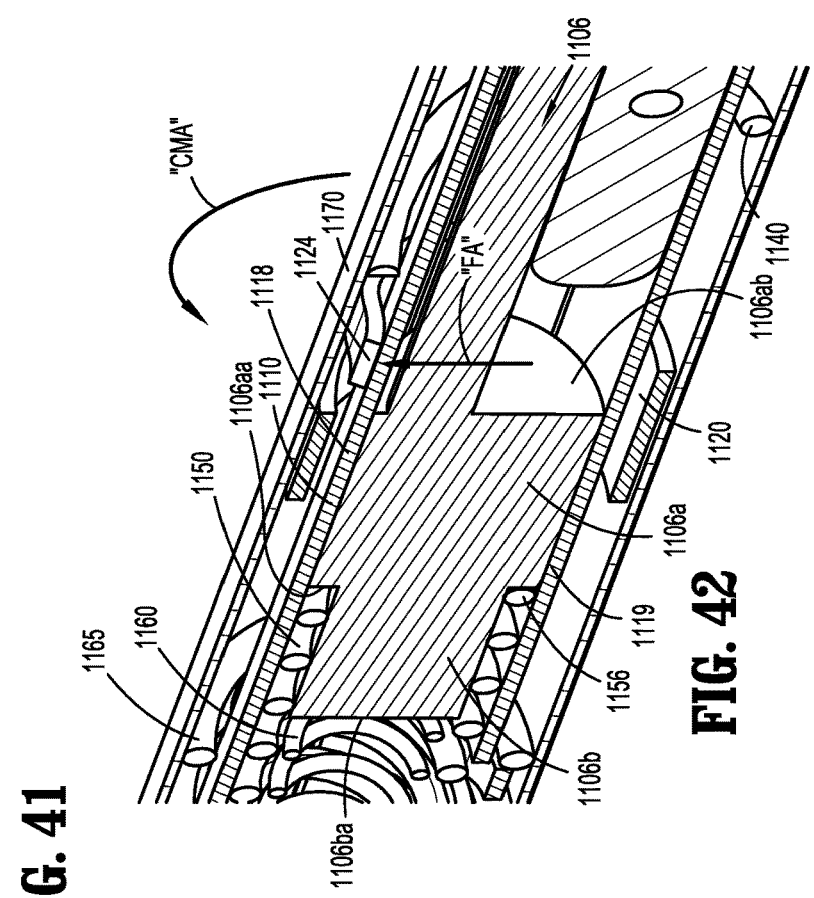
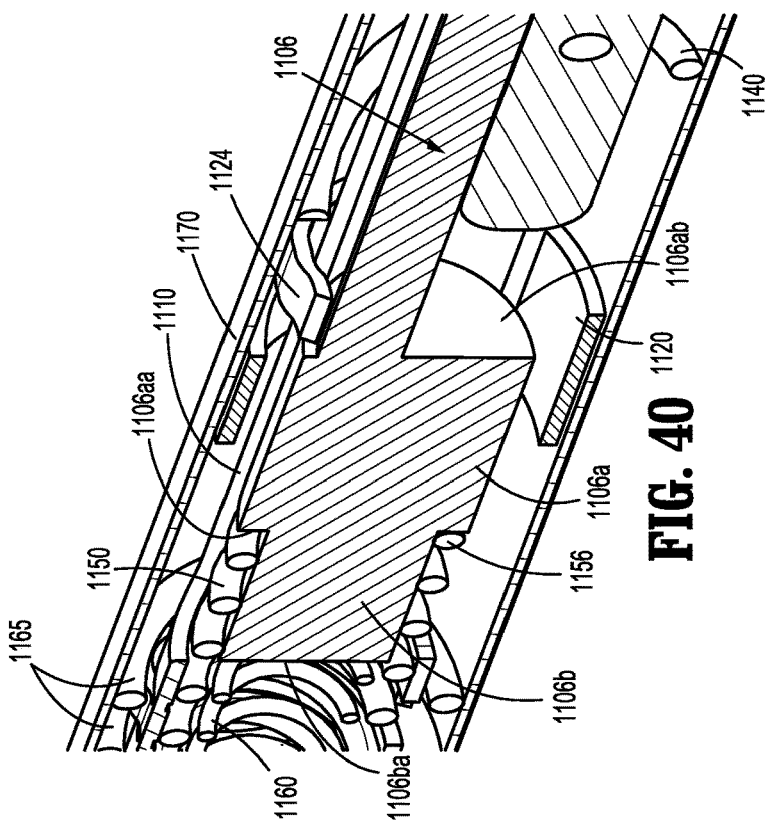
FIG. 41
FIG. 42
FIG. 40

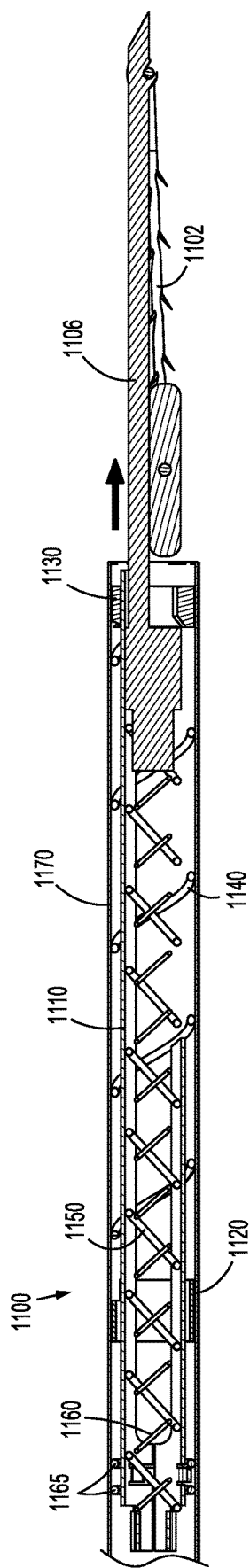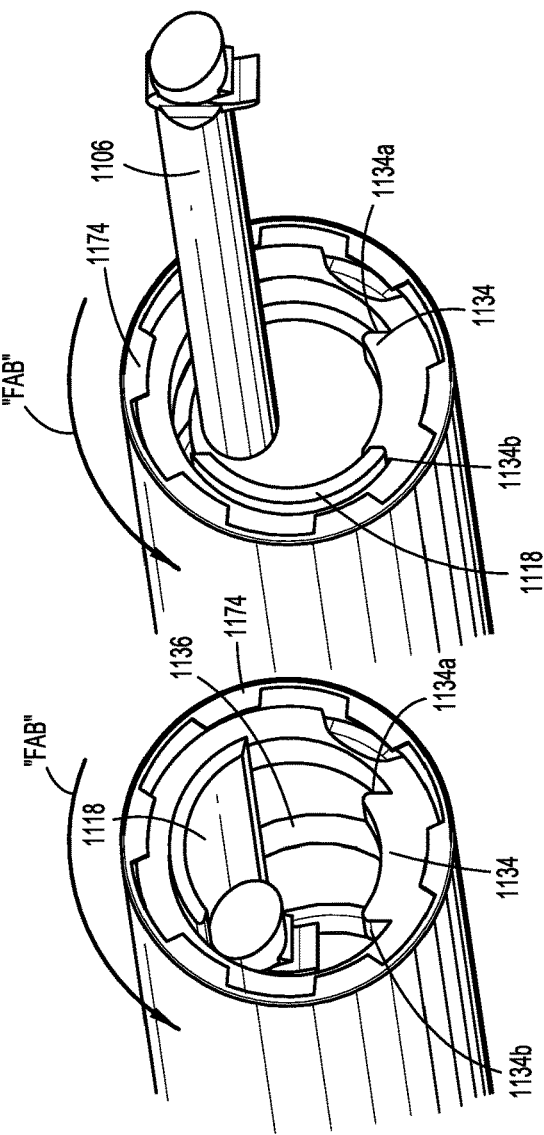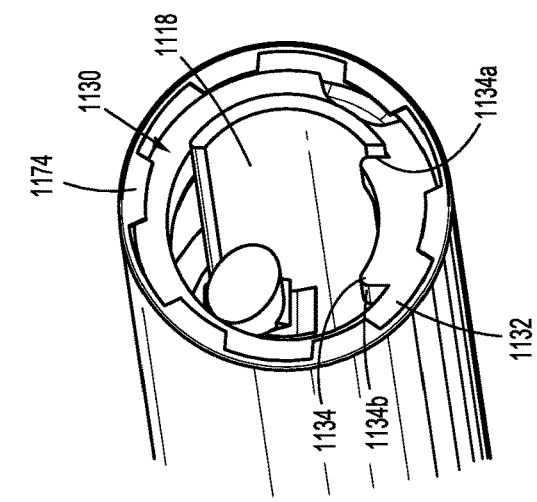
FIG. 43
FIG. 44
FIG. 45
FIG. 46

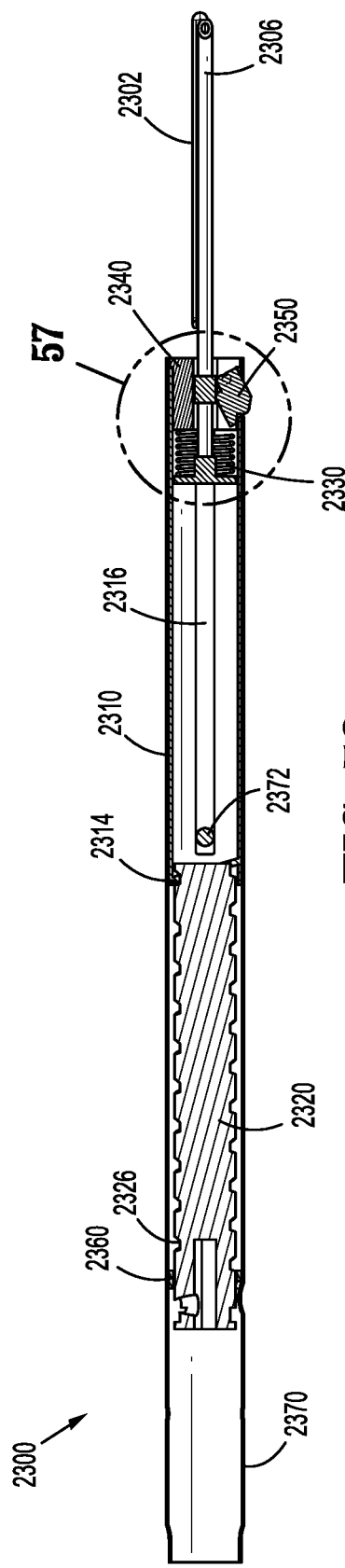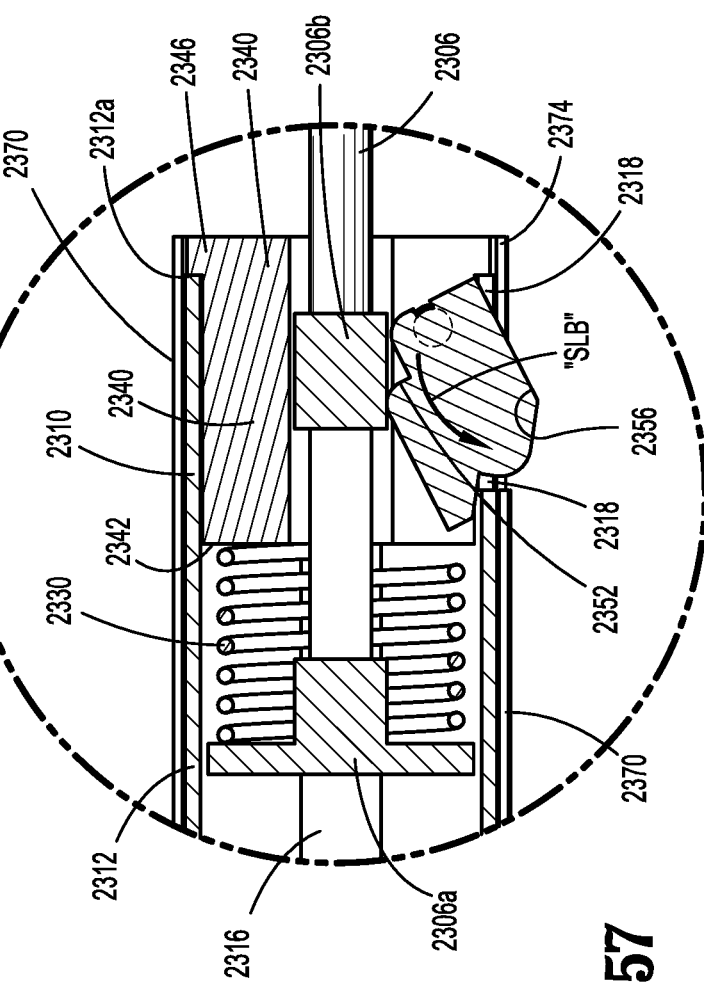
FIG. 56
FIG. 57

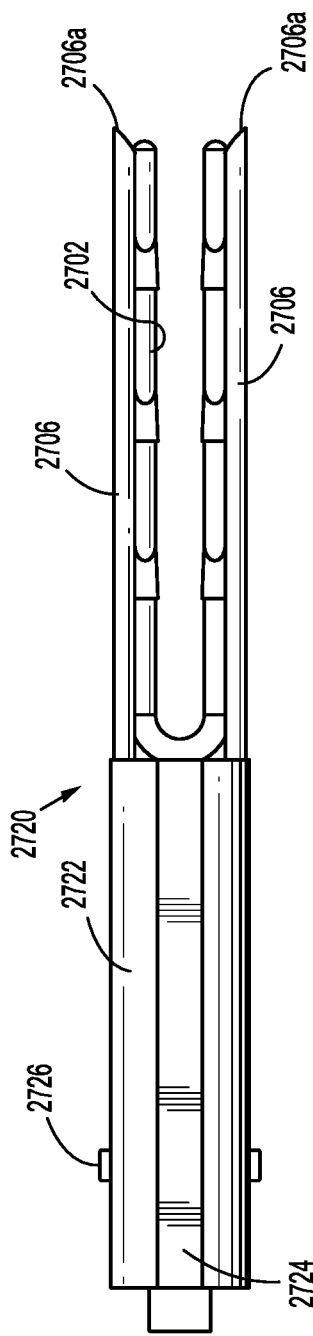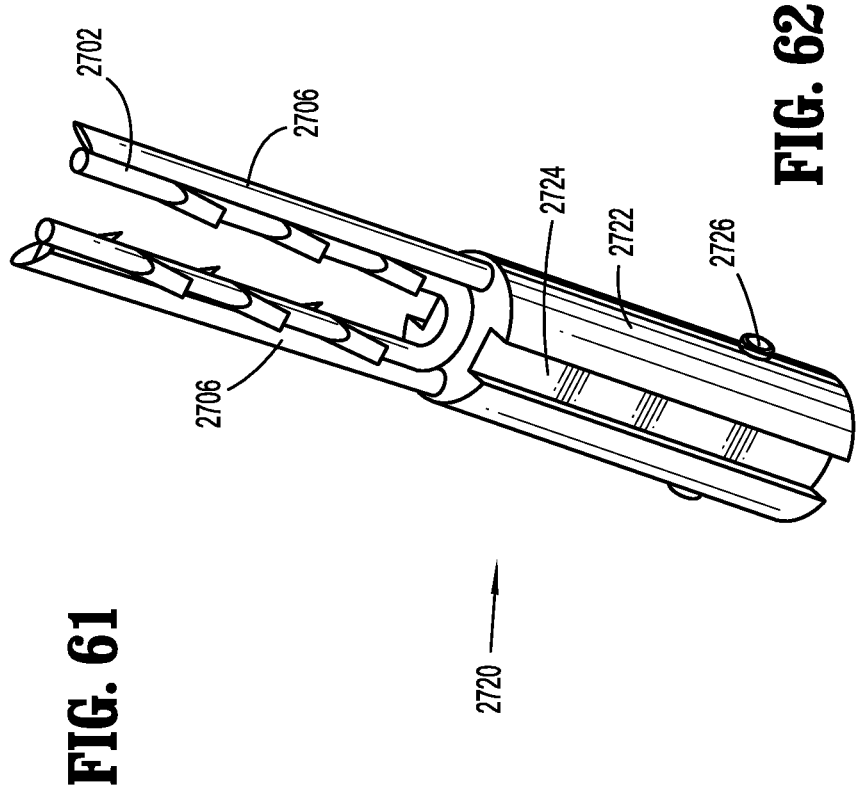
FIG. 61
FIG. 62

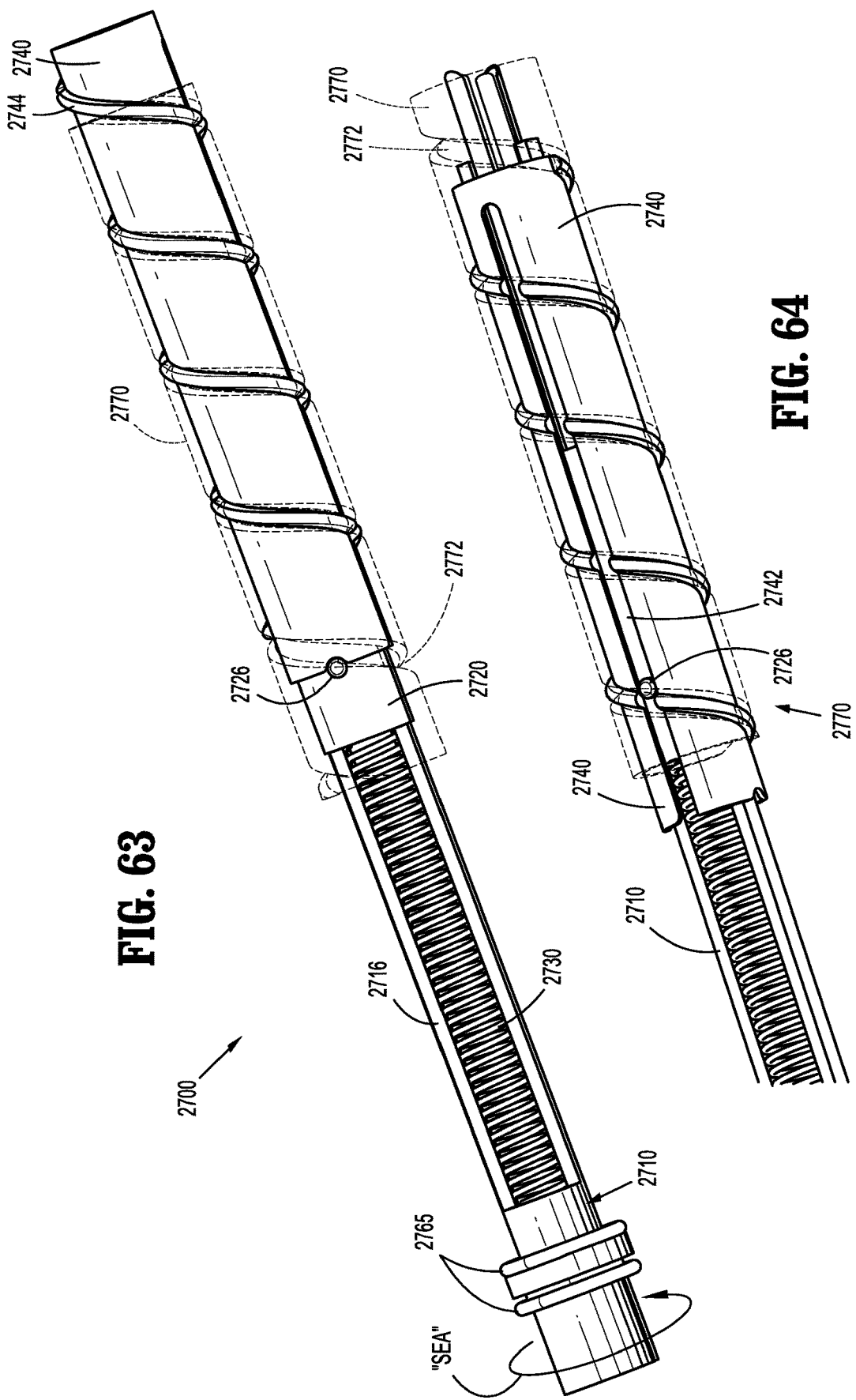

SURGICAL END EFFECTORS

CROSS-REFERENCE TO RELATED APPLICATIONS

This application claims the benefit of and priority to U.S. Provisional Patent Application No. 62/410,876 filed Oct. 21, 2016, the entire disclosure of which is incorporated by reference herein.

TECHNICAL FIELD

The present disclosure relates to end effectors for use with a surgical device for performing endoscopic surgical procedures and methods of use thereof. More specifically, the present disclosure relates to end effectors for advancing at least a portion of a needle into tissue.

BACKGROUND

During laparoscopic or endoscopic surgical procedures, access to a surgical site is achieved through a small incision or through a narrow cannula inserted through a small entrance wound in a patient. Several types of such surgical procedures include advancing at least part of a needle and/or suture into tissue. For example, it may be desired to insert a suture (e.g., a barbed suture) through an implant (e.g., mesh) and into tissue to help secure the implant to tissue. It may also be desired to replace suture that was previously inserted through the implant.

Additionally, after a needle is advanced into tissue, it may be desired to retract the needle in an outer tube of a surgical device or an end effector to prevent or minimize unintended contact between the needle and a physician, for instance.

Accordingly, a need exists for endoscopic surgical devices or end effectors for use therewith including the ability to advance and retract a needle into its outer tube.

SUMMARY

The present disclosure relates to an end effector for used with a surgical device. The end effector includes a drive assembly, a driver, a needle assembly, and a biasing element. The driver is disposed in mechanical cooperation with the drive assembly. Rotation of the drive assembly in a first direction causes distal translation of the driver with respect to the drive assembly. The needle assembly is disposed in mechanical cooperation with the driver. Distal translation of the driver causes a corresponding distal translation of the needle assembly. The biasing element is disposed in mechanical cooperation with the needle assembly. The biasing element is configured to bias the needle assembly proximally.

In disclosed embodiments, the biasing element includes a compression spring. It is further disclosed that the biasing element is disposed distally of a proximal base of the needle assembly.

In aspects of the present disclosure, the end effector also includes an end cap disposed adjacent a distal portion of the driver. The end cap is distally translatable with respect to the drive assembly.

It is also disclosed that the end effector includes a lock disposed in mechanical cooperation with a portion of the end cap. The lock may be configured to help prevent the needle assembly from moving proximally with respect to the driver until the needle assembly has reached a predetermined longitudinal position. In embodiments, the lock is pivotable with respect to the end cap. It is further disclosed that the lock is movable from a first position where a portion of the lock engages a portion of the needle assembly to a second position where the lock is free from engagement with the needle assembly. Additionally, it is disclosed that when the lock is in the first position, the lock resists a bias against the needle assembly provided by the biasing element, and when the lock is in the second position, the needle assembly is movable in a proximal direction with respect to the driver.

In a disclosed embodiment, the end effector includes an outer tube disposed radially outward of the driver. Engagement between a portion of the lock and an inner wall of the outer tube prevents the lock from moving toward the second position.

It is further disclosed that the driver includes a distal slot configured to allow a portion of the lock to pass therethrough.

It is also disclosed that the drive assembly includes a helical groove configured to engage a portion of the driver. Additionally, the drive assembly is fixed from longitudinal movement with respect to the outer tube.

In disclosed embodiments, the needle assembly includes a first needle extending distally from a needle block, and second needle extending distally from the needle block. The first needle is parallel to the second needle.

It is further disclosed that the end effector includes a suture disposed in mechanical cooperation with a needle of the needle assembly.

The present disclosure also relates to an end effector for use with a surgical device, where the end effector includes a drive assembly, a needle assembly, a helix assembly, and biasing element. The needle assembly is disposed in mechanical cooperation with the drive assembly. Rotation of the drive assembly in a first direction causes a corresponding rotation of the needle assembly. The needle assembly includes a pin. The helix assembly is disposed in mechanical cooperation with the needle assembly, and includes a proximal end and a longitudinal slot. The biasing element is disposed in mechanical cooperation with the needle assembly and is configured to bias the needle assembly distally with respect to the drive assembly. The needle assembly is movable with respect to the helix assembly from a first position where the pin is out of alignment with the longitudinal slot of the helix assembly, to a second position where the pin is aligned with the longitudinal slot of the helix assembly, to a third position where the pin has been distally translated with respect to the helix assembly.

In disclosed embodiments, a predetermined amount of rotation of the drive assembly with respect to the helix assembly causes a corresponding rotation of the needle assembly with respect to the helix assembly such that the needle assembly moves from its first position to its second position.

It is further disclosed that when the needle assembly is in the first position, engagement between the pin of the needle assembly and the proximal end of the helix assembly prevents the needle assembly from moving distally with respect to the drive assembly. Additionally, when the needle assembly is in the second position, the biasing element causes the pin to move distally within the longitudinal slot of the helix assembly such that the needle assembly is moved to the third position.

It is also disclosed that rotation of the drive assembly when the needle assembly is in the third position causes the helix assembly to rotate with respect to an outer tube. It is further disclosed that rotation of the helix assembly with respect to the outer tube causes proximal movement of the needle assembly with respect to the outer tube.

In disclosed embodiments, the drive assembly includes a first arm and a second arm. Each of the first arm and the second arm is configured to directly contact the needle assembly.

It is further disclosed that the end effector includes a suture disposed in mechanical cooperation with a needle of the needle assembly.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIGS. 1 and 2 are perspective views of a surgical device including an end effector engaged therewith according to embodiments of the present disclosure;

FIG. 3 is an enlarged view of the indicated area of detail of FIG. 2;

FIGS. 5-8 illustrate various types of needles and sutures in accordance with embodiments of the present disclosure;

FIGS. 9-20 illustrate various embodiments showing a needle engaged with a suture in accordance with embodiments of the present disclosure;

FIG. 25 is a perspective view of portions of the end effector of FIGS. 21-24;

FIG. 26 is an enlarged view of the area of detail indicated in FIG. 25;

FIG. 27 is an enlarged view of the area of detail indicated in FIG. 25;

FIG. 28 is a perspective view of portions of the end effector of FIGS. 21-27;

FIG. 29 is a perspective view of the needle of FIG. 28;

FIG. 31 is a perspective view of portions of the end effector of FIGS. 21-30;

FIG. 32 is an enlarged view of the area of detail indicated in FIG. 31;

FIG. 33 is an enlarged view of the area of detail indicated in FIG. 31;

FIG. 34 is a perspective view of an end effector in accordance with embodiments of the present disclosure;

FIGS. 35 and 36 are cut-away views of portions of the end effector of FIG. 34;

FIG. 40 is a cut-away view of a portion of the end effector of FIGS. 38 and 39;

FIG. 41 is a cross-sectional view of the end effector of FIGS. 38-40;

FIG. 42 is a cut-away view of a portion of the end effector of FIGS. 38-41;

FIG. 43 is a cross-sectional view of the end effector of FIGS. 38-42 illustrating a needle in an advanced position;

FIGS. 44-46 are cut-away view of a portion of the end effector of FIGS. 38-43 during different stages of operation;

FIG. 56 is a cross-sectional view of the end effector of FIGS. 50-55 illustrating a needle in an advanced position;

FIG. 57 is an enlarged view of the area of detail indicated in FIG. 56;

FIG. 61 is a side view of a needle assembly of the end effector of FIGS. 59-60;

FIG. 62 is a perspective view of the needle assembly of FIG. 61;

FIGS. 63 and 64 are perspective views of the end effector of FIGS. 59-62 shown during different stages of operation;

DETAILED DESCRIPTION OF EMBODIMENTS

Figure 1:
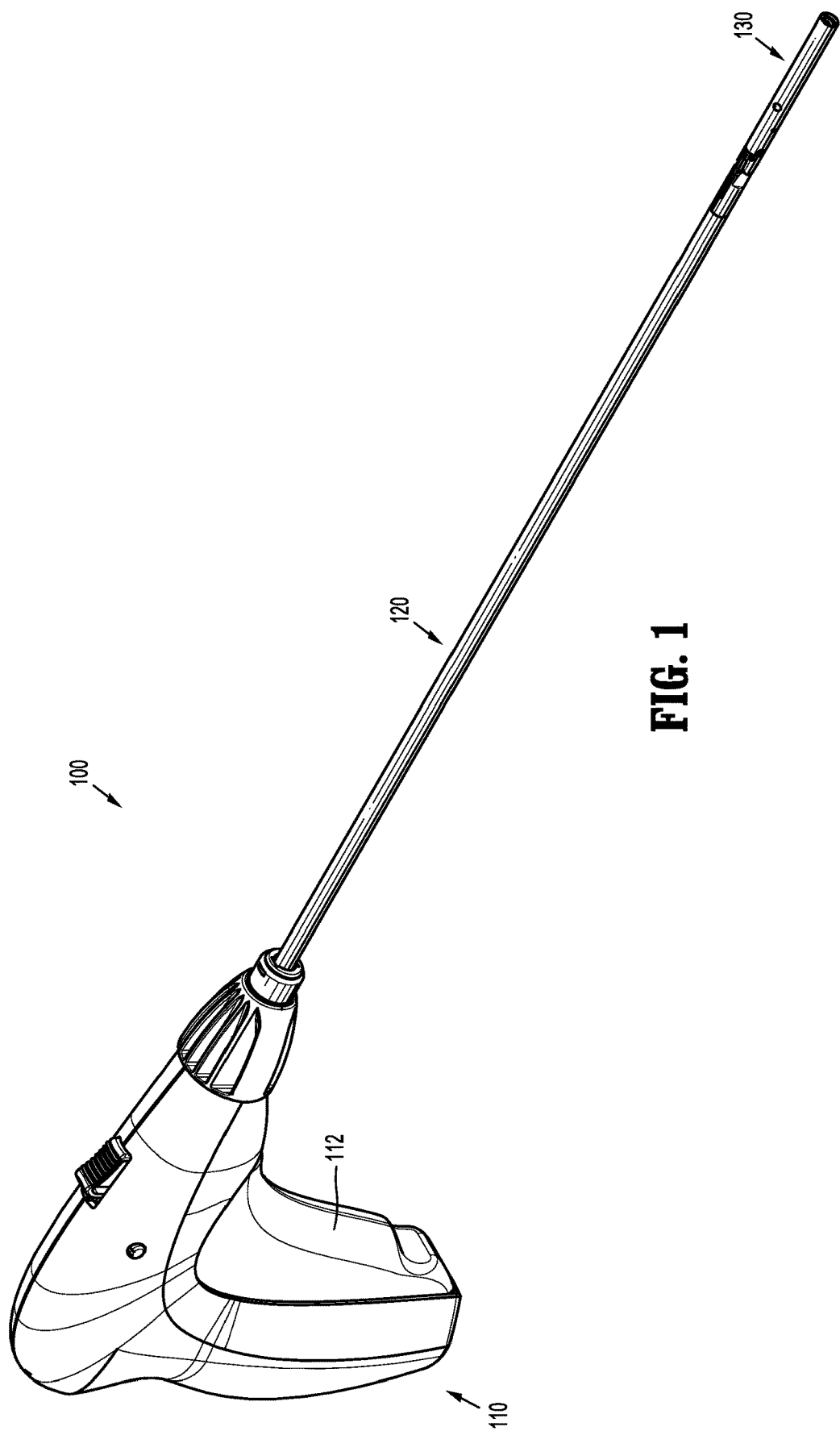
Figure 4:
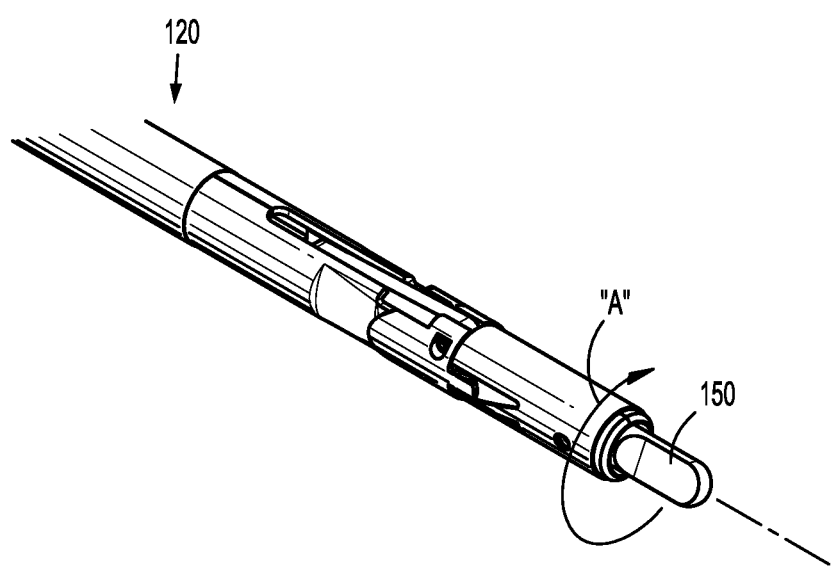
FIG. 4 is a perspective view of a distal portion of an elongated portion of the surgical device of FIGS. 1-3.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device that is farther from the user, while the term "proximal" refers to that portion of the surgical device that is closer to the user.

Non-limiting examples of surgical devices which may include articulation joints according to the present disclosure include manual, mechanical and/or electromechanical surgical tack appliers (i.e., tackers), clip appliers, surgical forceps, and the like.

Referring initial to FIGS. 1-4, a surgical instrument for use with the various end effectors of the present disclosure is generally designated as surgical device 100. Surgical device 100 includes a handle assembly 110, an elongated portion 120 extending distally from handle assembly 110, an end effector 130 disposed in mechanical cooperation (e.g., releasably engaged) with a distal portion of elongated portion 120, and a drive rod 150 disposed at least partially within elongated portion 120 and configured to engage (e.g., releasably engage) end effector 130. For clarity, FIGS. 1-3 illustrate a general end effector 130; various other end effectors are shown and described throughout this application and are configured for use with surgical device 100. Generally, end effector 130 is a separable component that is able to be used with a surgical instrument (e.g., a surgical fixation device handle). After its use (e.g., after one or more barbed sutures are released therefrom), the end effector 130 can be removed from the remainder of the surgical instrument, and a new or reloaded end effector 130 can then engage the surgical instrument and be used.

Handle assembly 110 includes a trigger or an actuator 112 (e.g., button, switch, etc.) thereon. In general, actuation of actuator 112 results in rotation of drive rod 150, e.g., in the general direction of arrow "A" in FIG. 4. There are a variety of ways surgical device 100 can transfer the movement caused by actuation of actuator 112 to rotation of drive rod 150, such as those disclosed in U.S. patent application Ser. No. 15/049,511, filed on Feb. 22, 2016, the entire contents of which are hereby incorporated by reference herein.

Several of the end effectors of the present disclosure are usable to advance at least a portion of a needle and/or at least a portion of a suture (e.g., a barbed suture) or other fixation device into tissue and/or mesh, for instance. An example of a disclosed use of the end effectors relates to positioning and/or fixation of laparoscopic ventral mesh. In such procedures, stay-sutures are typically tied to the corners and/or cardinal points by surgeons. The mesh and sutures are then rolled and introduced through the trocar and into the laparoscopic working space. The mesh is then unrolled, and positioned into place. If the sutures have needles attached, care must be taken during rolling, insertion, unrolling and positioning to help ensure the needle points do not damage the mesh (especially if the mesh includes an adhesion barrier layer) or to injure the patient or clinician. Once the mesh is properly unrolled and placed against the abdominal wall in the correct location, the stay-sutures are delivered across the abdominal wall (either from the inside toward the outside using an attached needle, or from the outside toward the inside using a suture passer introduced from outside the abdominal wall to grasp and pull the suture from the laparoscopic working space). After the stay-sutures have all been inserted, the clinician can finish fixating the mesh to the abdominal wall with a separate fixation device, such as a surgical tack applier.

The various end effectors disclosed herein help standardize surgical procedures (e.g., positioning and/or fixation of laparoscopic ventral mesh) and reduce the number of steps and time required to fixate the mesh with stay-sutures. The needle assemblies of the present disclosure allow a surgeon to introduce and pass a stay-suture through the implant and abdominal wall without the need to pre-attach the stay-sutures to needles, and without the risk of accidental needle sticks. The disclosed end effectors can used as a reload for use with standard surgical device handles to minimize the number of surgical devices (and the expense) needed for related surgical procedures.

Needle Styles

A variety of different types of needles may be used in combination with various embodiments of the present disclosure. While FIGS. 5-8 illustrate several types of needles, other types of needles may be used with the various end effectors disclosed herein. FIG. 5 illustrates a single needle 3000a extending from a needle block 3002, and a barbed suture 3010a operatively engaged (e.g., releasably engaged) therewith such that needle 3000a and barbed suture 3010a are insertable into an implant/tissue, and barbed suture 3010a remains in engagement with the implant/tissue when needle 3000a is retracted. A pledget 3003a is also included adjacent proximal portions of needle 3000a and barbed suture 3010a, which may releasably hold barbed suture 3010a, and which may act as a stop to help limit the distal advancement of barbed suture 3010a into the implant/tissue. A distal portion of barbed suture 3010a may be bent into a hollow cavity at a distal portion of needle 3000a to help releasably retain barbed suture 3010a in engagement with needle 3000a. FIG. 6 illustrates a pair of needles 3000b disposed in a parallel relationship extending from needle block 3002, and a suture 3010b supported between needles 3000b. Each needle of pair of needles 3000b extends distally from needle block 3002 in a direction that is perpendicular to a distal face 3002b of needle block 3002 (e.g., parallel to a longitudinal axis defined by an elongated portion of surgical device 100 engaged with needle block 3002). Pair of needles 3000b is sufficiently sturdy to support suture 3010b therebetween. A distal portion of suture 3010b may be bent into a hollow cavity at a distal portion of needle 3000b to help releasably retain suture 3010b in engagement with needles 3000b. It is envisioned that an adhesive is used to temporarily retain suture 3010b in the illustrated position. In use, at least a portion of needles 3000b and suture 3010b are inserted into/through an implant/tissue to emplace suture 3010b through the implant, for example. Suture 3010b remains emplaced through the implant up retraction of needles 3000b. Another suture 3010b can then be positioned between needles of pair of needles 3000b to allow for repeated use of pair of needles 3000b. FIG. 7 illustrates a pair of needles 3000c disposed in a bowed relationship extending from needle block 3002, and a suture 3010c supported between needles 3000c. Needles 3000c extend radially outward from each other, such that distal ends 3002c of needles 3000c are farther apart than proximal ends 3004c of needles 3000c. Pair of needles 3000c is sufficiently sturdy to support suture 3010c therebetween. A distal portion of suture 3010c may be bent into a hollow cavity at a distal portion of needle 3000c to help releasably retain suture 3010c in engagement with needles 3000c. It is envisioned that an adhesive is used to temporarily retain suture 3010c in the illustrated position. FIG. 8 illustrates a pair of needles 3000d extending in an arcuate manner from needle block 3002, and supporting a suture 3010d at least partially therebetween. Further, distal portions of suture 3010d are engaged with distal portions of needles 3000d. A distal portion of suture 3010d may be bent into a hollow cavity at a distal portion of needle 3000d to help releasably retain suture 3010d in engagement with needles 3000d. It is envisioned that an adhesive is used to temporarily retain suture 3010d in the illustrated position. Pair of needles 3000d may be used when a clinician desires to secure a relatively wide portion of an implant or tissue, as the distal tips of needles 3000*d* are positioned far away from each other, with respect to pair of needles 3000*b* and 3000*c*. It is envisioned that needles 3000*a*, 3000*b*, 3000*c* and 3000*d* are made from a shape memory material, such as nitinol.

Needle Tip Attachment

Several different ways of coupling needles with suture are usable with embodiments of end effectors disclosed herein and are illustrated in FIGS. 9-20. In FIG. 9, a needle 4010 is shown including a flange 4012 projecting from a recess 4014 within a shaft of needle 4010. A distal end of flange 4012 may be able to move, flex or pivot away from recess 4014. A barbed suture 4000 is releasably held by flange 4012. In use, distal advancement of needle 4010 towards (e.g., into) tissue causes a corresponding distal advancement of barbed suture 4000. When needle 4010 is moved proximally or retracted, flange 4012 moves over or releases barbed suture 4000, thus leaving barbed suture 4000 within tissue, for example.

In FIGS. 10-11, a needle 4020 is shown including an actuation suture 4022 extending through needle 4020 between a recess 4024 within a shaft of needle 4020 and a proximal opening 4026 of needle 4020. A distal portion of actuation suture 4022 releasably holds barbed suture 4000. In use, distal advancement of needle 4020 towards (e.g., into) tissue causes a corresponding distal advancement of barbed suture 4000. When actuation suture 4022 is moved proximally or retracted in the general direction of arrow "NTA," distal portion of actuation suture 4022 moves in the general direction of arrow "NTB" or releases barbed suture 4000, thus leaving barbed suture 4000 within tissue, for example. It is envisioned that a proximal portion of actuation suture 4022 is engaged with an appropriate anchor portion of an end effector such that advancement of needle 4020 moves needle 4020 away from the anchor portion of the end effector, which causes a relative retraction of actuation suture 4022.

In FIGS. 12-13, a needle 4030 is shown including a suture 4002 engaged with a cavity 4032 of needle 4030. Cavity 4032 of needle 4030 includes a first, proximal portion 4032*a* and a second, distal portion 4032*b*. As shown, distal portion 4032*b* of cavity 4032 is deeper than proximal portion 4032*a* of cavity 4032. Distal portion 4032*b* of cavity 4032 is configured to releasably engage an enlarged or ball portion 4002*a* of suture 4002, and proximal portion 4032*a* of cavity 4032 is configured to releasably engage a body portion 4002*b* of suture 4002. In use, distal advancement of needle 4030 towards (e.g., into) tissue causes a corresponding distal advancement of suture 4002. When needle 4030 is moved proximally or retracted, suture 4002 is able to slide in the general direction of arrow "NTA" relative to needle 4030, thus leaving suture 4002 within tissue, for example.

Figure 15:
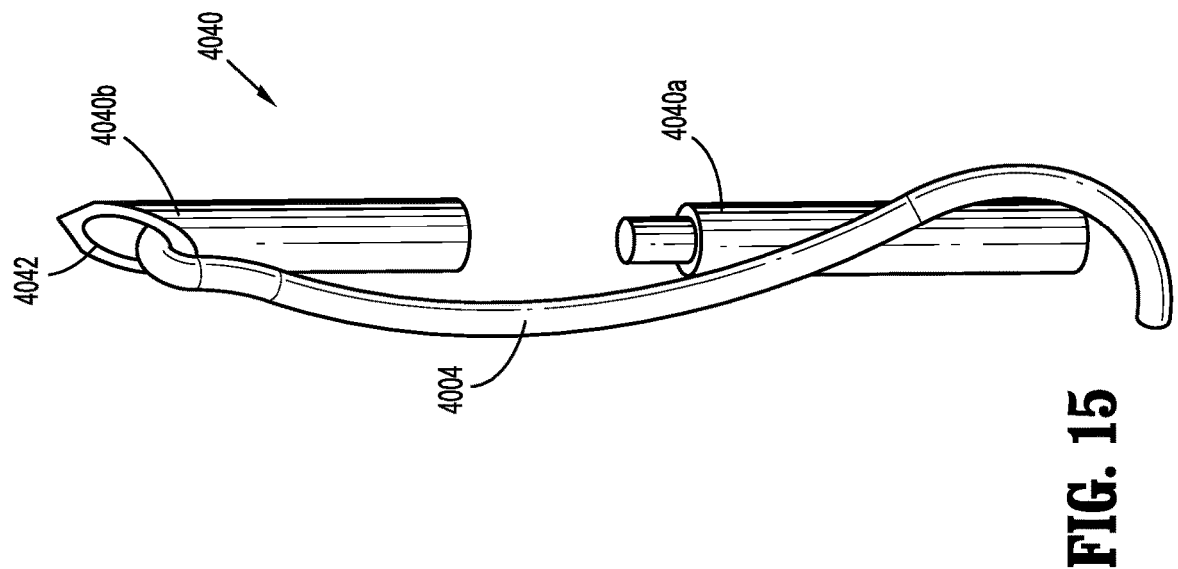
Figure 14:
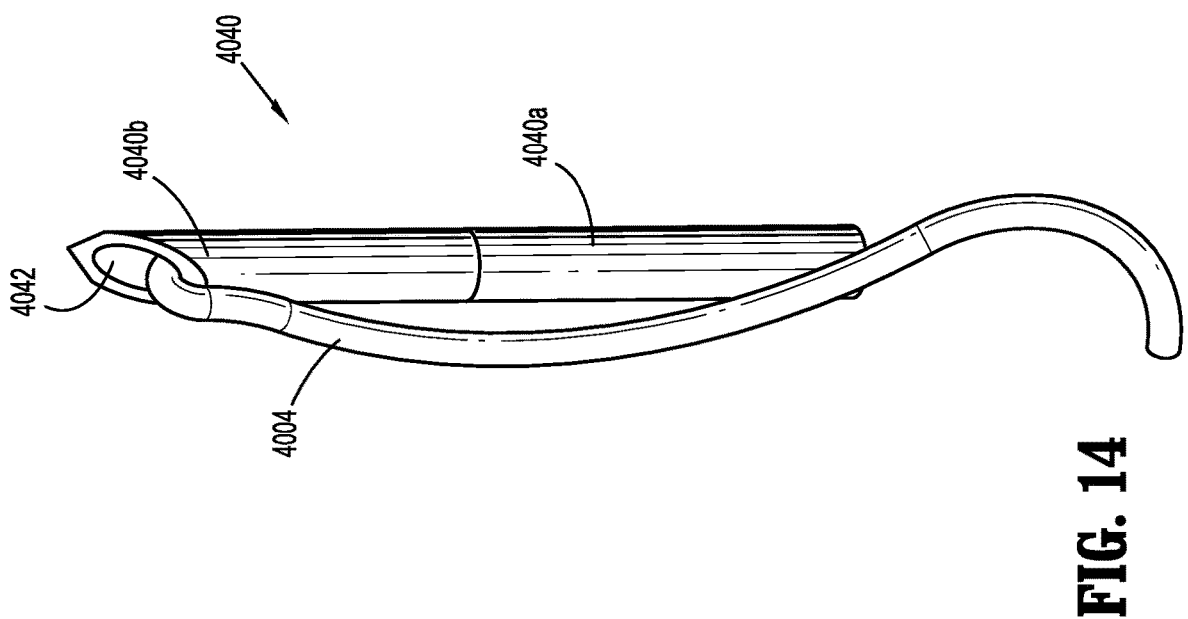

In FIGS. 14-15, a needle 4040 is shown including a proximal portion 4040*a* and a distal portion 4040*b*. Proximal portion 4040*a* and distal portion 4040*b* of needle 4040 are releasably engaged with each other. Accordingly, moving proximal portion 4040*a* proximally with respect to distal portion 4040*b*, for example, can separate the two portions of needle 4040. A suture 4004 is engaged with a distal part of distal portion 4040*b* of needle 4040. For example, a portion of suture 4004 is disposed within a cavity 4042 of distal portion 4040*b* of needle 4040. In use, distal advancement of needle 4040 towards (e.g., into) tissue causes a corresponding distal advancement of suture 4004. When proximal portion 4040*a* of needle 4040 is moved proximally or retracted, distal portion 4040*b* of needle 4040 separates from proximal portion 4040*a*, which results in distal portion 4040*b* of needle 4040 and portions of suture 4004 remaining in tissue.

In FIG. 16, a needle 4050 is shown including an angled axial cut 4052 disposed therein. Angled axial cut 4052 of needle 4050 is configured to frictionally and releasably hold a portion of suture 4004 therein. In use, distal advancement of needle 4050 towards (e.g., into) tissue causes a corresponding distal advancement of suture 4004. When needle 4050 is moved proximally or retracted, portions of suture 4004 release from angled axial cut 4052 and remain within tissue, for example. It is envisioned that needle 4050 may be manufactured using an angled mill.

In FIG. 17, a needle 4060 is shown including a perpendicular axial cut 4062 disposed therein. Perpendicular axial cut 4062 of needle 4060 is configured to frictionally and releasably hold a portion of suture 4004 therein. In use, distal advancement of needle 4060 towards (e.g., into) tissue causes a corresponding distal advancement of suture 4004. When needle 4060 is moved proximally or retracted, portions of suture 4004 release from perpendicular axial cut 4062 and remain within tissue, for example. It is envisioned that needle 4060 may be manufactured using a cut off wheel.

In FIG. 18, a needle 4070 is shown including a lateral aperture 4072 disposed therethrough. Lateral aperture 4072 of needle 4070 is configured to allow a portion of suture 4004 to be threaded therethrough. In use, distal advancement of needle 4070 towards (e.g., into) tissue causes a corresponding distal advancement of suture 4004. When needle 4070 is moved proximally or retracted, portions of suture 4004 are removed from lateral aperture 4072 and remain within tissue, for example. It is envisioned that a pin or wire travels through needle 4070 to sever suture 4004.

In FIGS. 19 and 20, a needle 4080 is shown including a slotted tip 4082. Slotted tip 4082 of needle 4080 is configured to frictionally and releasably hold a portion of suture 4004 (FIG. 19) or multiple sutures (FIG. 20) therein. In use, distal advancement of needle 4080 towards (e.g., into) tissue causes a corresponding distal advancement of suture(s) 4004. When needle 4080 is moved proximally or retracted, portions of suture(s) 4004 are removed from slotted tip 4082 and remain within tissue, for example.

Spring Loaded Safety Cover

Referring now to FIGS. 21-33, an embodiment of an end effector 1000 including a spring-loaded safety cover assembly is shown. End effector 1000 is configured for use in connection with surgical device 100. Generally, end effector 1000 is configured to prevent unintentional contact with a needle and/or a barbed suture within or extending distally from its outer tube. While FIGS. 21-33 illustrate a particular type of barbed suture 1002 and a particular type of needle 1006, end effector 1000 may be used with different types of sutures and/or needles.

Figure 21:
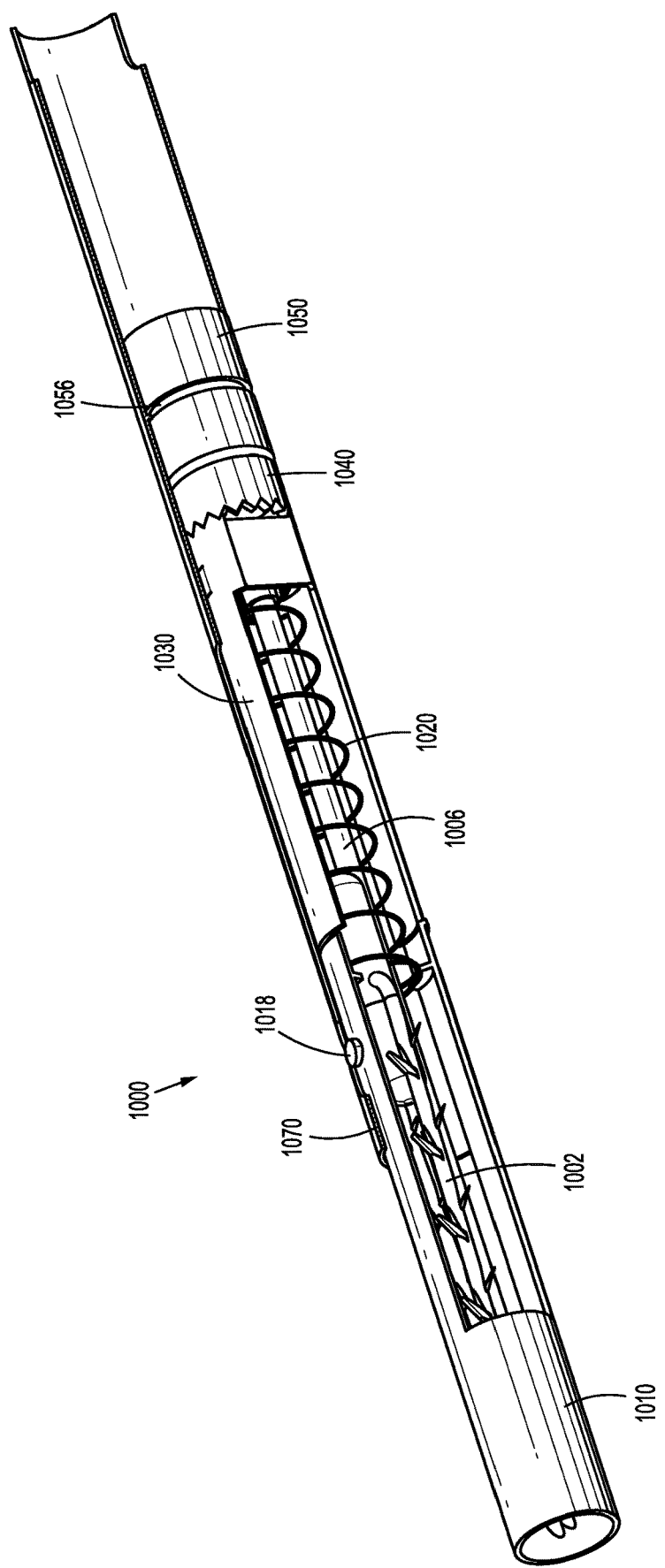
FIG. 21 is a perspective view of portions of an end effector in accordance with embodiments of the present disclosure.
Figure 22:
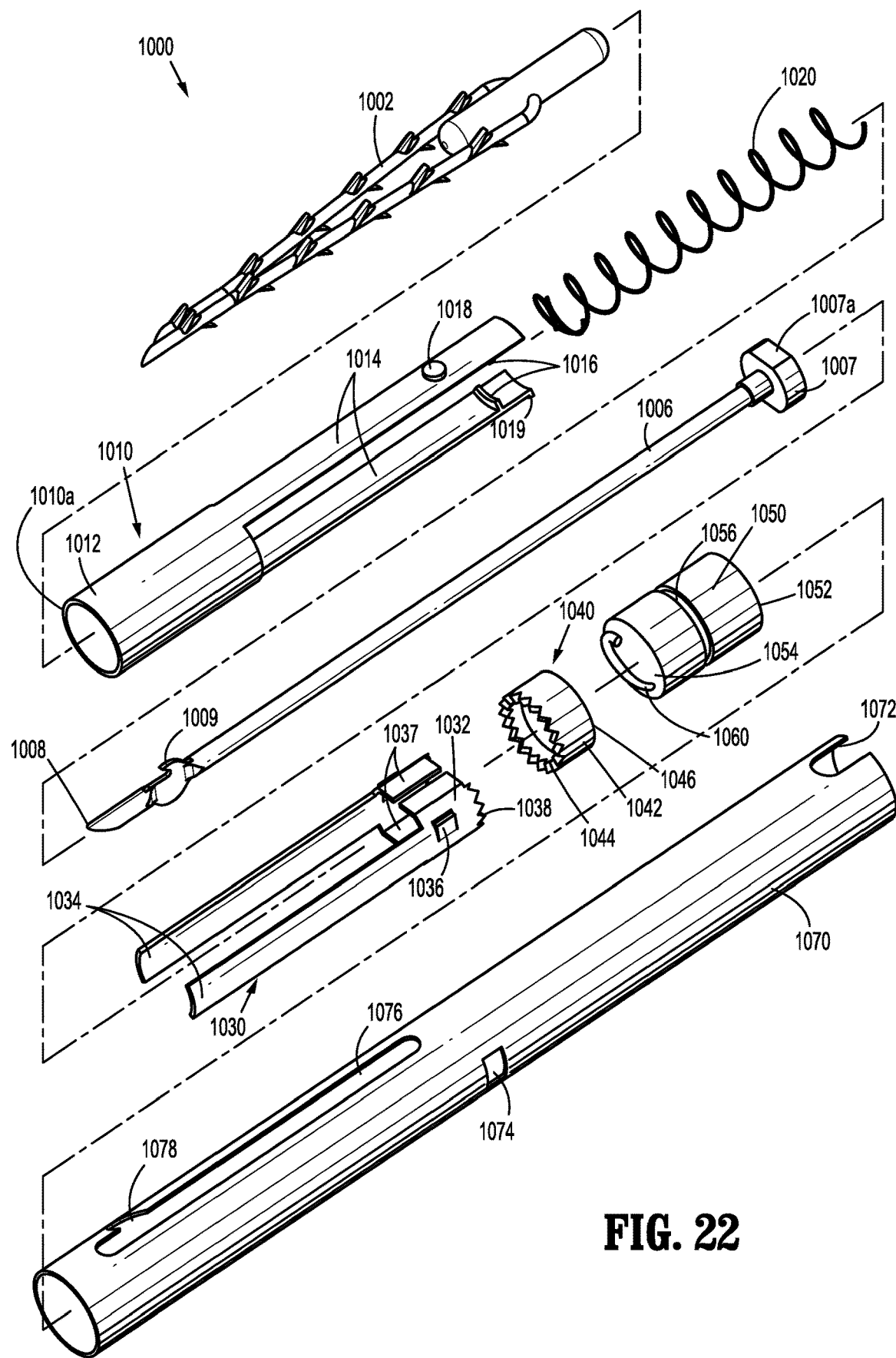
FIG. 22 is an assembly view of the end effector of FIG. 21.

With particular reference to FIGS. 21 and 22, end effector 1000 includes a cover 1010, a first biasing element or spring 1020, a clevis 1030, a clutch 1040, a drive element 1050, a second biasing element or spring 1060 (FIG. 22), and an outer tube 1070.

Cover 1010 of end effector 1000 includes a cylindrical body portion 1012, a pair of arms 1014 extending proximally from body portion 1012, a lip 1016 extending radially inward from a proximal portion of each arm 1014, and a tab 1018 extending radially outward from a proximal portion of one the arms 1014.

Clevis 1030 of end effector 1000 includes a body portion 1032, a pair of arms 1034 extending distally from body portion 1032, a flange 1036 extending radially outward from body portion 1032, and a plurality of teeth 1038 disposed on a proximal end of body portion 1032. First biasing element 1020 is positioned between arms 1034 of clevis 1030 and arms 1014 of cover 1010. Body portion 1032 of clevis 1030 engages a proximal end of first biasing element 1020; lips 1016 of cover 1010 engage a distal end of first biasing element 1020.

A proximal portion 1007 of needle 1006 is positioned radially inward of body portion 1032 of clevis 1030. Further, flat portions 1007a (see FIG. 28) of proximal portion 1007 of needle 1006 engage corresponding flat portions 1037 of body portion 1032 of clevis 1030, thus limiting or preventing rotation therebetween. Needle 1006 also includes a distal tip 1008 and a hook 1009. Distal tip 1008 of needle 1006 is configured to pierce tissue, and hook 1009 of needle 1006 is configured to engage a portion of barbed suture 1002.

Clutch 1040 of end effector 1000 includes a body portion 1042, a plurality of teeth 1044 disposed on a distal end of body portion 1042, and a proximal surface 1046. Teeth 1044 of clutch 1040 are configured to engage teeth 1038 of clevis 1030.

Drive element 1050 of end effector 1000 is mechanically engaged (e.g., operatively coupled, directly affixed, etc.) to drive rod 150 of surgical device 100 of the present disclosure. Drive element 1050 includes a proximal end 1052, a distal end 1054, and a groove 1056. Groove 1056 of drive element 1050 is configured to engage a shipping wedge (not shown) to help lock drive element 1050 in place with respect to outer tube 1070, for example. Proximal end 1052 of drive element 1050 is configured to engage the drive rod. Distal end 1054 of drive element 1050 is mechanically engaged with second biasing element 1060. Proximal surface 1046 of clutch 1040 is positioned to engage second biasing element 1060. That is, second biasing element 1060 is positioned between proximal surface 1046 of clutch 1040 and distal end 1054 of drive element 1050.

Outer tube 1070 of end effector 1000 includes a proximal notch 1072, a cutout 1074, and a longitudinal groove 1076 having an angled slot 1078 extending therefrom. Outer tube 1070 is configured for positioning radially outward of, and to at least partially contain, at least portions of barbed suture 1002, needle 1006, cover 1010, first biasing element 1020, clevis 1030, clutch 1040, drive element 1050, and second biasing element 1060.

Figure 23:
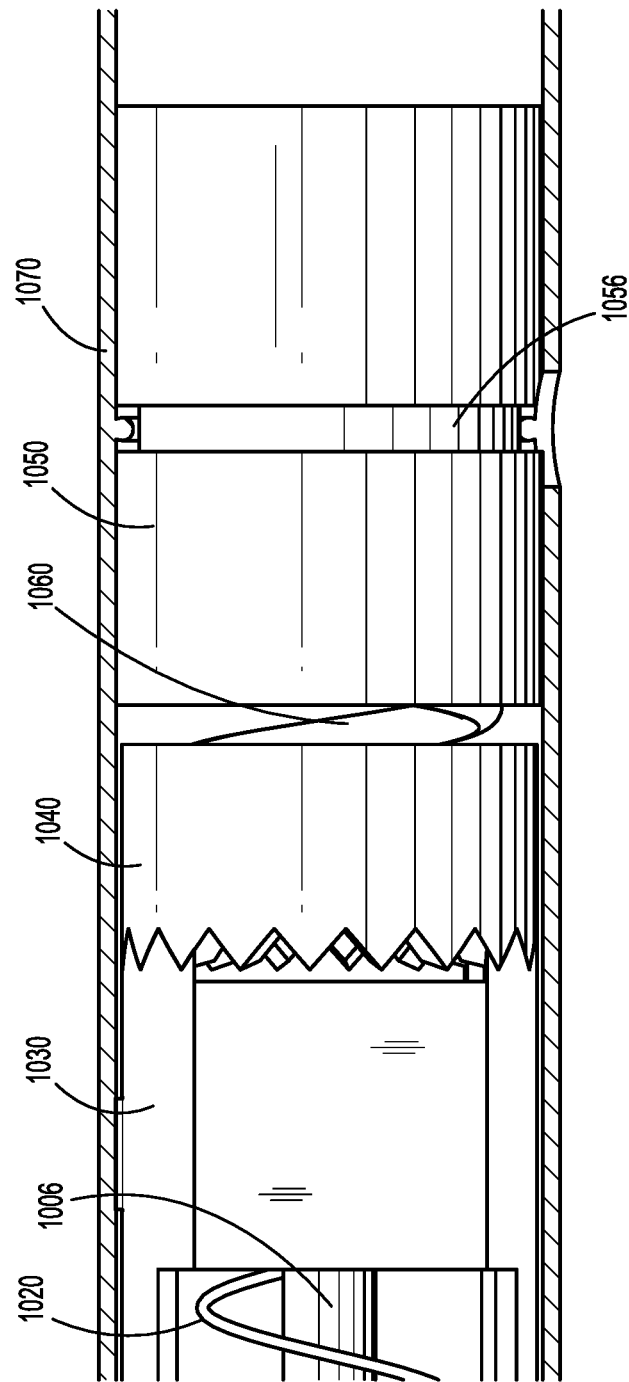
FIG. 23 is a cross-sectional view of a portion of the end effector of FIGS. 21 and 22.

As shown in FIG. 23, prior to use, a portion of proximal notch 1072 is longitudinally aligned with groove 1056 of drive element 1050 such that a shipping wedge (not shown) can extend through proximal notch 1072 and into engagement with groove 1056. The engagement between drive element 1050, second biasing element 1060, clutch 1040, and clevis 1030 is also shown in FIG. 23. As shown, second biasing element 1060 is disposed between drive element 1050 and clutch 1040, thus transferring rotational movement from drive element 1050 (and drive rod 150, as discussed above) to clutch 1040. Additionally, second biasing element 1060 enacts a distal force onto clutch 1040 to help maintain engagement between teeth 1044 of clutch 1040 and teeth 1038 of clevis 1030. Accordingly, rotation of clutch 1040 results in a corresponding rotation of clevis 1030.

Figure 24:
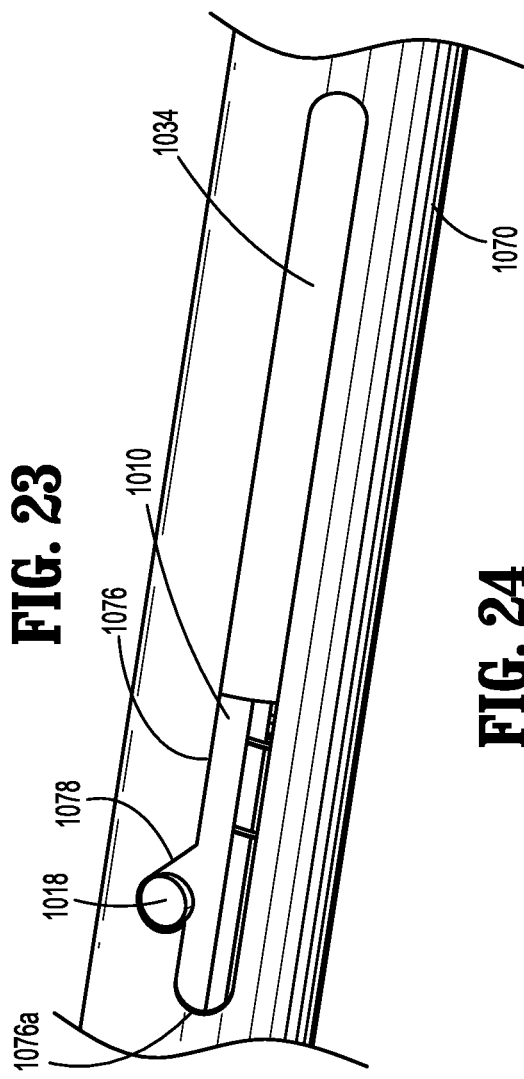
FIG. 24 is a perspective view of a portion of the end effector of FIGS. 21-23.
Figure 30:
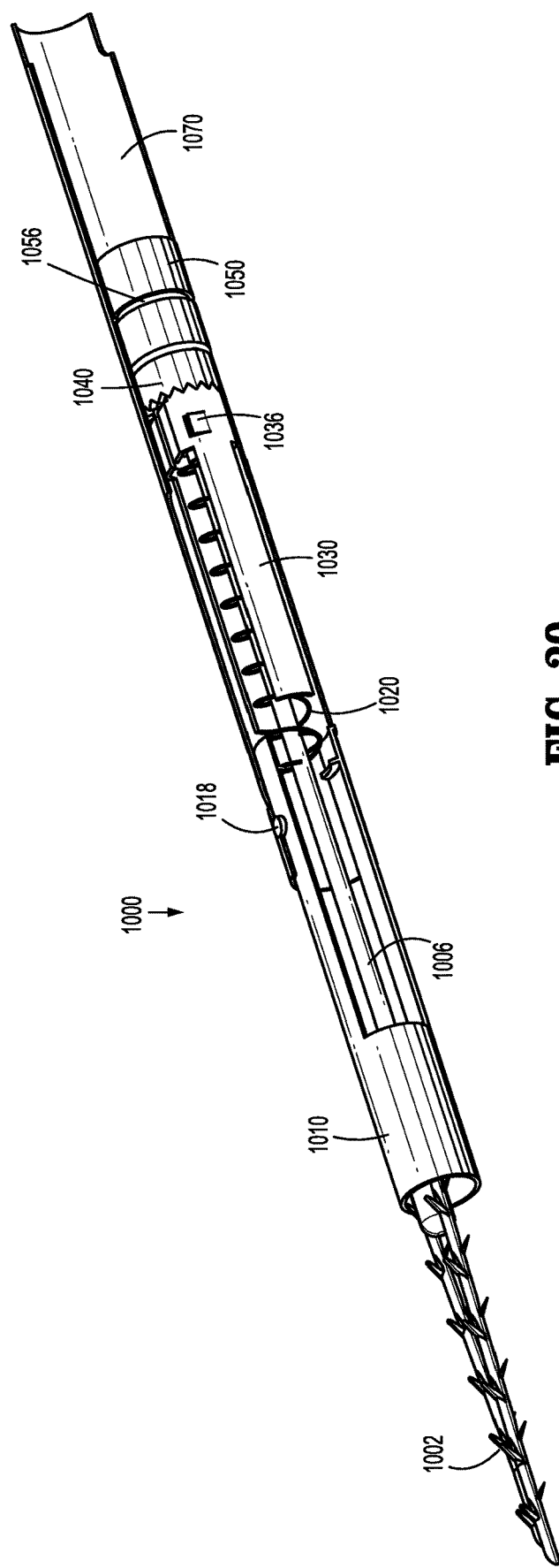
FIG. 30 is a perspective view of portions of the end effector of FIGS. 21-27 and with a needle in an advanced position.

With particular reference to FIG. 24, prior to use, tab 1018 of cover 1010 of end effector 1000 is disposed within angled slot 1078 of longitudinal groove 1076 of outer tube 1070. The engagement between tab 1018 and angled slot 1078 prevents cover 1010 from distally advancing with respect to outer tube 1070. In this position, cover 1010 is in its distal-most position where it radially surrounds distal tip 1008 of needle 1006 and barbed suture 1002.

In use, in response to at least a partial actuation of the trigger, the drive rod 150 rotates, as discussed above. Rotation of the drive rod results in a corresponding rotation of drive element 1050, clutch 1040, and clevis 1030. A predetermined amount of rotation (e.g., about) 90° of clevis 1030 causes flange 1036 of clevis 1030 to rotate in the general direction of arrow "FLA" from a first position within cutout 1074 of outer tube 1070, to a second position where flange 1036 engages a lateral wall 1074a of cutout 1074 of outer tube 1070 (see FIG. 27). Engagement between flange 1036 and lateral wall 1074a prevents continued rotation of clevis 1030 with respect to outer tube 1070 in the direction of arrow "FLA." Accordingly, when clevis 1030 continues to rotate in the direction of arrow "FLA" (e.g., in response to continued or additional actuation of the trigger), outer tube 1070 also rotates in the direction of arrow "FLA" with respect to cover 1010.

Rotation of outer tube 1070 in the direction of arrow "FLA" with respect to cover 1010 causes angled slot 1078 of outer tube 1070 to disengage from tab 1018 of cover 1010, which causes tab 1018 of cover 1010 to be within longitudinal groove 1076 of outer tube 1070. When tab 1018 of cover 1010 is within longitudinal groove 1076 of outer tube 1070, cover 1010 is in an unlocked position.

Next, a user presses a distal tip of surgical device 100 against tissue and/or mesh to emplace barbed suture 1002 at least partially therein and/or therethrough. More particularly, the user pushes a distal edge 1010a of cover 1010 against the tissue/mesh, which causes cover 1010 to move proximally with respect to outer tube 1070 against the bias of first biasing element 1020. As cover 1010 moves proximally, tab 1018 of cover 1010 travels proximally within longitudinal groove 1076 of outer tube 1070. The proximal movement of cover 1010 exposes barbed suture 1002 and distal tip 1008 of needle 1006, at least portions of which extend distally beyond outer tube 1070, and enables barbed suture 1002 and distal tip 1008 to penetrate the tissue/mesh.

As the user moves the surgical device 100 proximally (e.g., after barbed suture 1002 has been emplaced in tissue/mesh), first biasing element 1020 urges cover 1010 distally with respect to outer tube 1070. Cover 1010 continues to move distally while tab 1018 of cover 1010 travels within longitudinal groove 1076 of outer tube 1070 until tab 1018 contacts a distal edge 1076a of longitudinal groove 1076, preventing further distal movement of cover 1010 with respect to outer tube 1070 (see FIGS. 31 and 32). Further, as tab 1018 of cover 1010 contacts distal edge 1076a of longitudinal groove 1076, at least one proximal finger 1019 of cover 1010 enters an aperture 1071 of outer tube 1070 (e.g., in response to a radial outward bias of arms 1014), thus effectively locking the longitudinal position of cover 1010 with respect to outer tube 1070 (see FIGS. 31 and 33).

Folding Safety Cover

With reference to FIGS. 34-37, a safety cover assembly 2800 for use with various end effectors disclosed herein is shown. A cover 2810 of safety cover assembly 2800 is configured to pivot between a first position where safety cover 2800 helps prevent unintentional contact with a needle 2806 (FIG. 34), and a second position where safety cover 2800 allows needle 2806 to be driven into tissue (FIG. 35).

Figure 37:
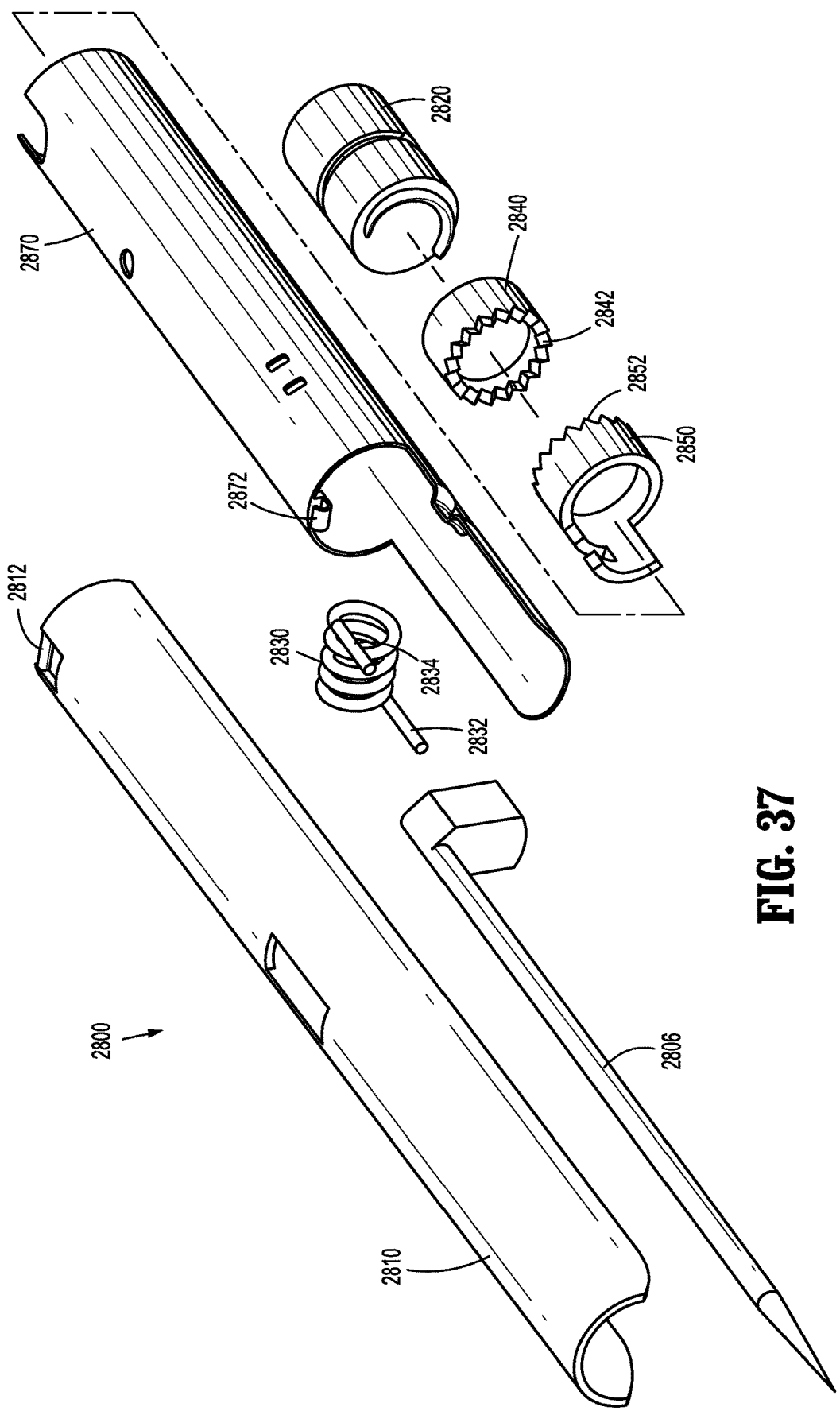
FIG. 37 is an assembly view of the end effector of FIGS. 34-36.
Figure 38:
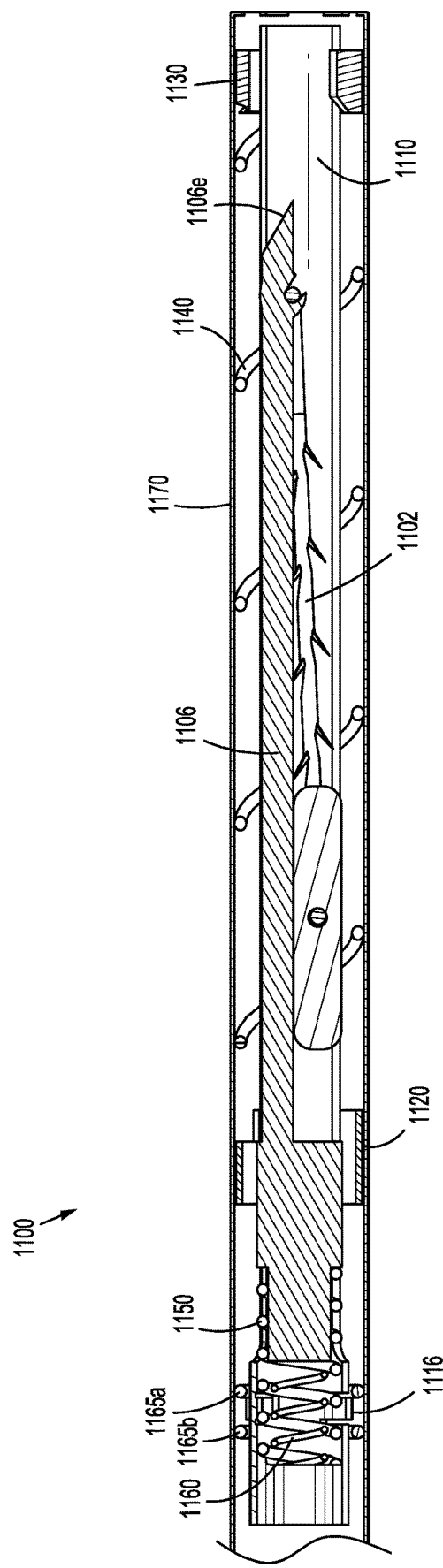
FIG. 38 is a cross-sectional view of an end effector in accordance with embodiments of the present disclosure.

With particular reference to FIG. 37, safety cover assembly 2800 includes cover 2810, a drive member 2820, a biasing member 2830, a gear 2840, a clutch 2850, and an outer tube 2870. Cover 2810 includes a proximal lip 2812, and an angled blocking portion 2814 (FIG. 36). Proximal lip 2812 is configured to pivotably engage a distal finger 2872 of outer tube 2870 to facilitate pivotal movement therebetween. Blocking portion 2814 of cover 2810 is configured to selectively engage a portion of needle 2806 and/or clutch 2850. The engagement between blocking portion 2814 and needle 2806 and/or clutch 2850 restricts the biasing force supplied by biasing member 2830.

Biasing member 2830 of cover assembly 2800 includes a first portion 2832 engaged with (e.g., affixed to) a proximal portion of needle 2086, and a second portion 2834 engaged with (e.g., affixed to) a proximal portion of cover 2810. Biasing member 2830 is configured to bias cover 2810 away from needle 2806 toward its second position (FIG. 35). As noted above, the engagement between blocking portion 2814 of cover 2810 and needle 2806 and/or clutch 2850 resists the biasing force supplied by biasing member 2830.

Drive member 2820, gear 2840, and clutch 2850 of cover assembly 2800 are disposed radially within outer tube 2870. Drive member 2820 is mechanically engaged (e.g., operatively coupled, directly affixed, etc.) to drive rod 150 of surgical device 100 of the present disclosure. Accordingly, rotation of the drive rod 150 in the general direction of arrow "FSA" results in a corresponding rotation of drive member 2820. Additionally, drive member 2820 is configured to engage gear 2840 such that rotation of drive member 2820 in the general direction of arrow "FSA" causes a corresponding rotation of gear 2840 in the general direction of arrow "FSA." Further, gear 2840 is configured to engage clutch 2850 such that rotation of gear 2840 in the general direction of arrow "FSA" causes a corresponding rotation of clutch 2850.

With reference to FIGS. 35-37, clutch 2850 of cover assembly 2800 is configured to engage a portion of cover 2810, such that rotation of clutch 2850 in the general direction of arrow "FSA" causes a corresponding rotation of cover 2810 in the general direction of arrow "FSA." With particular reference to FIG. 36, rotation of cover 2810 in the general direction of arrow "FSA" causes blocking portion 2814 of cover 2810 to rotate with respect to needle 2806, such that blocking portion 2814 no longer resists the force exerted by biasing member 2830 onto cover 2810. Accordingly, rotation of drive rod 150 in the general direction of arrow "FSA" causes a corresponding rotation of drive member 2820, gear 2840, clutch 2850 and cover 2810, thus causing cover 2810 to pivot in the general direction of arrow "FSB" (FIG. 35) toward its second position, since blocking portion 2814 no longer resists the force exerted by biasing member 2830 onto cover 2810. Additionally, proximal teeth 2852 of clutch 2850, which mate with distal teeth 2842 of gear 2840, are configured to skip following additional rotation of gear 2840 after cover 2810 moves toward its second position.

When cover 2810 is in its second position, needle 2806 is exposed and is able to be driven into tissue, for example. If a user desires to move cover 2810 back toward its first position, the user may use a secondary instrument or the user's hand, to pivot cover 2810 toward its first position against the bias of biasing member 2830. The cover 2810 can be rotated in the general direction of arrow "FSC" (FIG. 35) such that blocking portion 2814 engages needle 2806 and resists the force exerted by biasing member 2830.

Preloaded Spring

Referring now to FIGS. 38-49, an embodiment of an end effector 1100 including a pre-loaded spring assembly is shown. End effector 1100 is configured for use in connection with surgical device 100. Generally, end effector 1100 is configured to advance a needle 1106 and to eject a barbed suture 1102 towards tissue. While FIGS. 38-49 illustrate a particular type of barbed suture 1102 and a particular type of needle 1106, end effector 1100 may be used with different types of sutures and/or needles.

Figure 39:
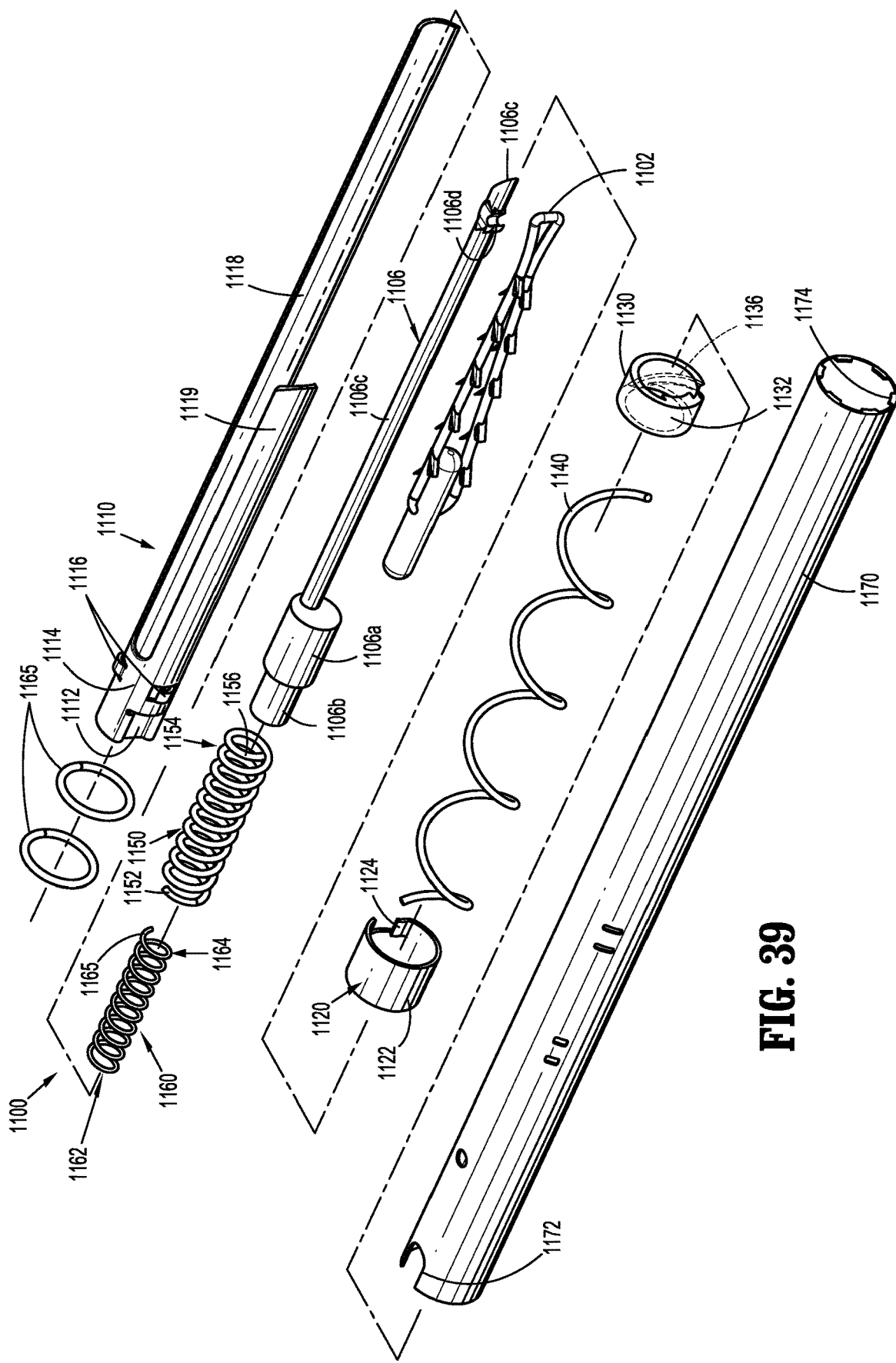
FIG. 39 is an assembly view of the end effector of FIG. 38.

With particular reference to FIG. 39, end effector 1100 includes a drive assembly 1110, a proximal stop 1120, a distal stop 1130, a helix or coil 1140, a first biasing element 1150, a second biasing element 1160, a pair of rings 1165, and an outer tube 1170.

Drive assembly 1110 of end effector 1100 is mechanically engaged (e.g., operatively coupled, directly affixed, etc.) to drive rod 150 of surgical device 100 of the present disclosure. Drive assembly 1110 includes a proximal portion 1112, a body portion 1114, members 1116, a first arm 1118 extending distally from body portion 1114, and a second arm 1119 extending distally from body portion 1114.

Proximal stop 1120 of end effector 1100 is positioned radially outward of body portion 1114 of drive assembly 1110, and includes a body portion 1122, and a finger 1124. Finger 1124 extends radially inward from body portion 1122, is movable in a radially outward direction with respect to body portion 1122, and may be biased radially inward. As discussed below, finger 1124 is configured to move between its first, radially inward position (FIG. 40) toward its second, radially outward position (FIG. 42) in response to contact by first arm 1118 and/or second arm 1119 of drive assembly 1110. Members 1116 of drive assembly 1110 are configured to retain the longitudinal position of drive assembly 1110 by being positioned proximally of a first ring 1165a and distally of a second ring 1165b (see FIG. 38).

Distal stop 1130 of end effector 1100 is positioned radially outward of at least part of first arm 1118 of drive assembly 1110, and includes a body portion 1132, a protrusion 1134 extending radially inward from body portion 1132, and a helical groove 1136 disposed within body portion 1132. With particular reference to FIGS. 44-46, protrusion 1134 of distal stop 1130 includes a first stop surface 1134a and a second stop surface 1134b, which are each configured to engage first arm 1118 of drive assembly 1110. Additionally, distal stop 1130 is rotationally supported within outer tube 1170.

Helix or coil 1140 of end effector 1100 extends between proximal stop 1120 and distal stop 1140 and radially within outer tube 1170. Helix or coil 1140 is stationary with respect to outer tube 1170, and is configured to engage helical groove 1136 of distal stop 1130 such that distal stop 1130 can move longitudinally and rotationally within outer tube 1170 and with respect to outer tube 1170.

Needle 1106 is disposed radially inward of drive assembly 1110, and includes a body portion 1106a, a proximal extension 1106b extending proximally from body portion 1106a, an elongated portion 1106c, a hook 1106d, and a distal tip 1106e. Body portion 1106a is configured to move longitudinally within outer tube 1170 and with respect to outer tube 1170. Distal tip 1106e of needle 1106 is configured to pierce tissue, and hook 1106d of needle 1106 is configured to engage a portion of barbed suture 1102.

First biasing element 1150, e.g., a compression spring, of end effector 1100 includes a proximal portion 1152 and a distal portion 1154. Proximal portion 1152 of first biasing element 1150 is positioned within body portion 1114 of drive assembly 1110. Distal portion 1154 of first biasing element 1150 is positioned radially outward of proximal extension 1106b of needle 1106. A distal end 1156 of first biasing element 1150 is positioned in contact with a proximal surface 1106aa of body portion 1106a of needle 1106. First biasing element 1150 is configured to bias needle 1106 distally with respect to outer tube 1170.

Second biasing element 1160, e.g., a compression spring, of end effector 1100 includes a proximal portion 1162 and a distal portion 1164. Proximal portion 1162 of second biasing element 1160 is positioned within body portion 1114 of drive assembly 1110. Distal portion 1164 of second biasing element 1160 is positioned proximally of proximal extension 1106*b* of needle 1106. A distal end 1166 of second biasing element 1160 is positioned in contact with a proximal surface 1106*ba* of proximal extension 1106*b* of needle 1106. Second biasing element 1160 is configured to bias needle 1106 distally with respect to outer tube 1170.

Rings 1165 (e.g., O-rings) of end effector 1100 are positioned radially outward of proximal body portion 1112 of drive assembly 1110. Rings 1165 help maintain appropriate spacing between drive assembly 1110 and outer tube 1170, and help facilitate rotation of drive assembly 1110 with respect to outer tube 1170.

Outer tube 1170 of end effector 1100 includes a proximal notch 1172, and a lip 1174 extending radially inward from a distal end of outer tube 1170. Outer tube 1170 is configured for positioning radially outward of, and for at least partially retaining, at least portions of barbed suture 1102, needle 1106, drive assembly 1110, proximal stop 1120, distal stop 1130, helix or coil 1140, first biasing element 1150, second biasing element 1160, and pair of rings 1165.

As shown in FIG. 40, prior to use, finger 1124 of proximal stop 1120 is in contact with a distal face 1106*ab* of body portion 1106*a* of needle 1106. This contact between finger 1124 and needle 1106 resists the distal bias of first biasing element 1150 and second biasing element 1160, and thus prevents needle 1106 from distally translating with respect to outer tube 1170.

In use, in response to at least a partial actuation of the trigger 112 of surgical device 100, drive rod 150 of surgical device 100 rotates, as discussed above. With reference to FIGS. 40-42, rotation of drive rod 150 results in a corresponding rotation of drive assembly 1110 of end effector 1100 with respect to outer tube 1170 and with respect to proximal stop 1120. A predetermined amount of rotation (e.g., about 90°) of drive assembly 1110 causes cam member 1116 of drive assembly 1110 to rotate in the general direction of arrow "CMA" (FIG. 42) from a first position where first arm 1118 and second arm 1119 are free from contact with finger 1124 of proximal stop 1120, to a second position where first arm 1118 and/or second arm 1119 engage(s) finger 1124. Engagement between first arm 1118 or second arm 1119 and finger 1124 causes finger 1124 to flex radially outward in the general direction of arrow "FA" in FIG. 42. Once finger 1124 has flexed or moved radially outward, finger 1124 no longer resists the distal bias of first biasing element 1150 and second biasing element 1160, thus resulting in needle 1106 distally translating with respect to outer tube 1170.

As needle 1106 travels distally, a distal portion of needle 1106 (e.g., distal tip 1106*e*) and barbed suture 1102 distally exit outer tube 1170, and engage tissue/mesh, for instance. Distal movement of needle 1106 with respect to outer tube 1170 continues until distal face 1106*ab* of body portion 1106*a* of needle 1106 contacts a proximal edge 1138 of distal stop 1130. Engagement between needle 1106 and distal stop 1130 resists the distal bias of first biasing element 1150 and second biasing element 1160, thus resulting in needle 1106 ceasing its distal travel with respect to outer tube 1170.

Additionally, and with reference to FIGS. 41 and 43-46, after drive assembly 1110 of end effector 1100 initially rotates (e.g., about 90°) and engages finger 1124 of proximal stop 1120, drive assembly 1110 continues to rotate (e.g., up to about 270°), and first arm 1118 thereof also rotates (in the general direction of arrow "FAB" in FIGS. 45 and 46) until first arm 1118 contacts second stop surface 1134*b* of protrusion 1134 of distal stop 1130. Continued rotation of drive assembly 1110, and thus its first arm 1118, causes a corresponding rotation of distal stop 1130 in the general direction of arrow "FAB."

Figure 47:
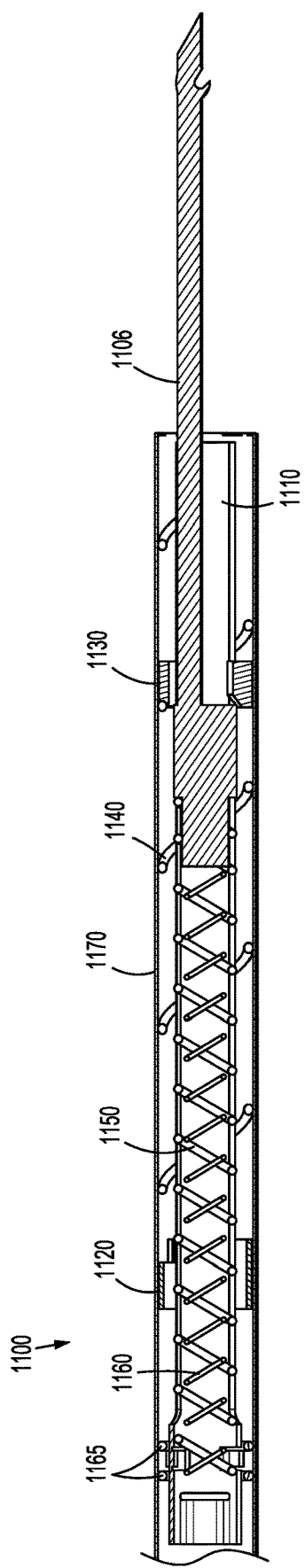
FIG. 47 is a cross-sectional view of the end effector of FIGS. 38-46 illustrating the needle in an advanced position.
Figure 48:
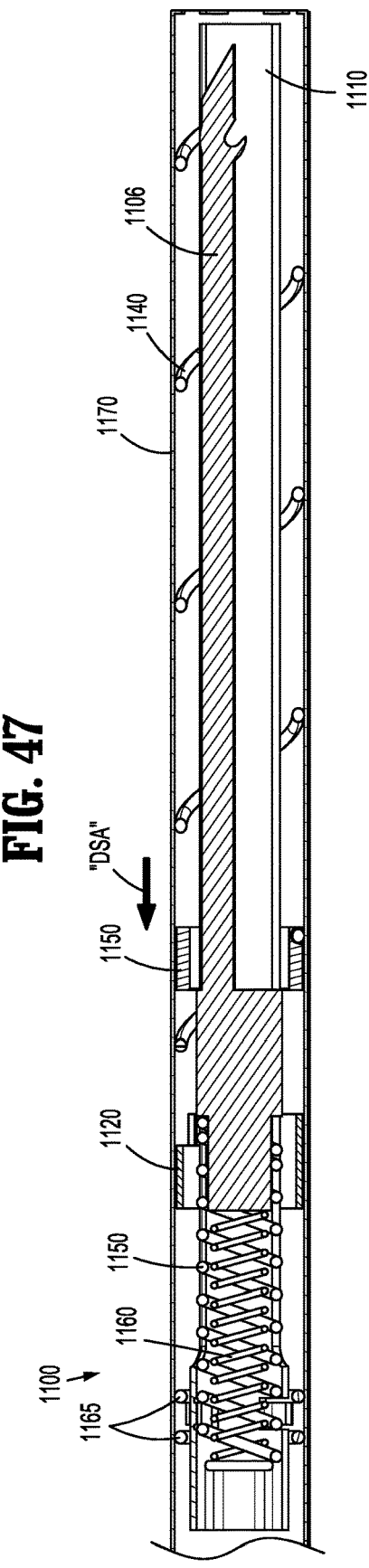
FIG. 48 is a cross-sectional view of the end effector of FIGS. 38-47 illustrating the needle in a retracted position.
Figure 49:
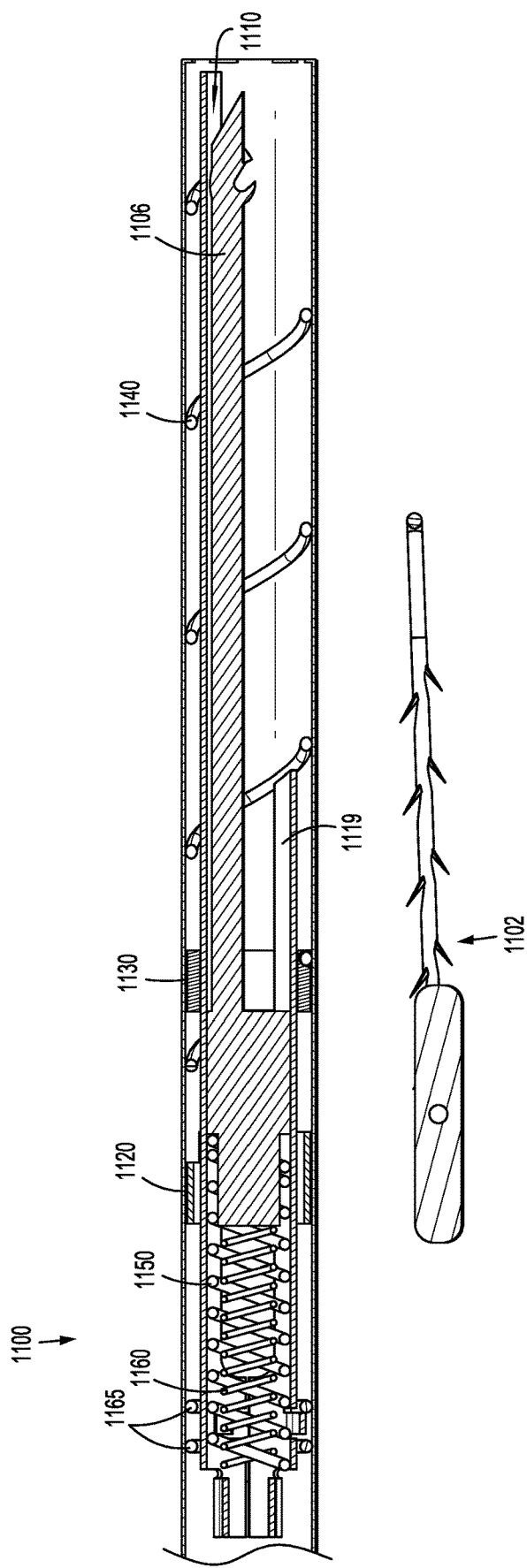
FIG. 49 is a cross-sectional view of the end effector of FIGS. 38-48 illustrating the needle in the retracted position and illustrating a barbed suture for use therewith.
Figure 50:
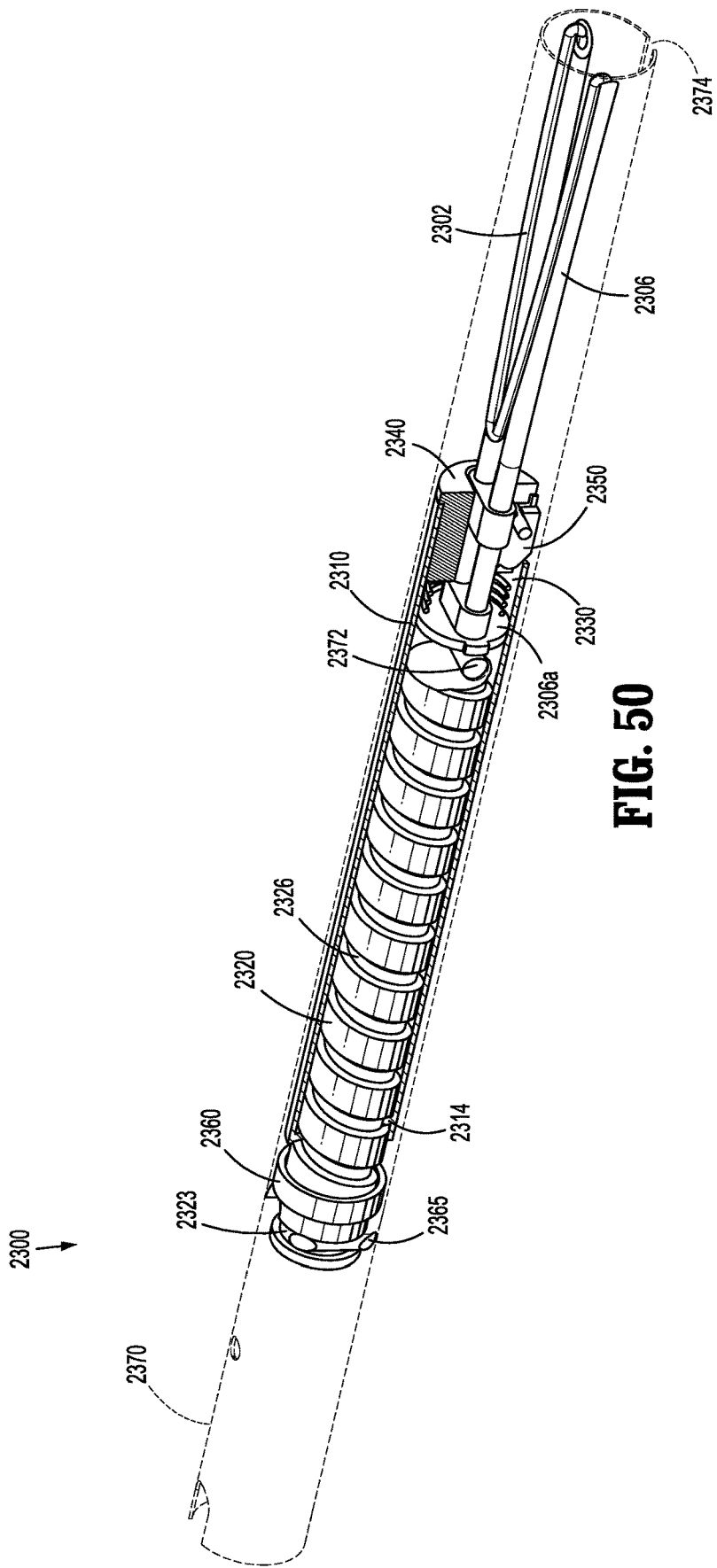
FIG. 50 is a perspective view of an end effector in accordance with embodiments of the present disclosure.

Referring now to FIGS. 47-49, the engagement between helical groove 1136 of distal stop 1130 and helix or coil 1140 causes rotation of distal stop 1130 in the general direction of arrow "FAB" (FIGS. 45 and 46) causes distal stop 1130 to move proximally with respect to outer tube 1170 in the general direction of arrow "DSA" (FIG. 48). As additionally shown, proximal movement of distal stop 1130 results in a corresponding proximal movement of needle 1106 due to the engagement between distal stop 1130 and distal face 1106*ab* of body portion 1106*a* of needle 1106. Needle 1106 is movable proximally until its distal tip 1106*e* is longitudinally aligned with or proximal of a distal end of outer tube 1170, thereby reducing the possibility of a user unintentionally contacting needle 1106.

Swing Lock Helix Drive

Referring now to FIGS. 50-58, an embodiment of an end effector 2300 is shown. End effector 2300 is configured for use in connection with surgical device 100. Generally, end effector 2300 is configured to advance a suture 2302 and a needle assembly including needle 2306 towards tissue. While FIGS. 50-58 illustrate a particular type of suture 2302 and needle 2306, end effector 2000 may be used with different types of sutures (e.g., barbed sutures) and needles.

Figure 51:
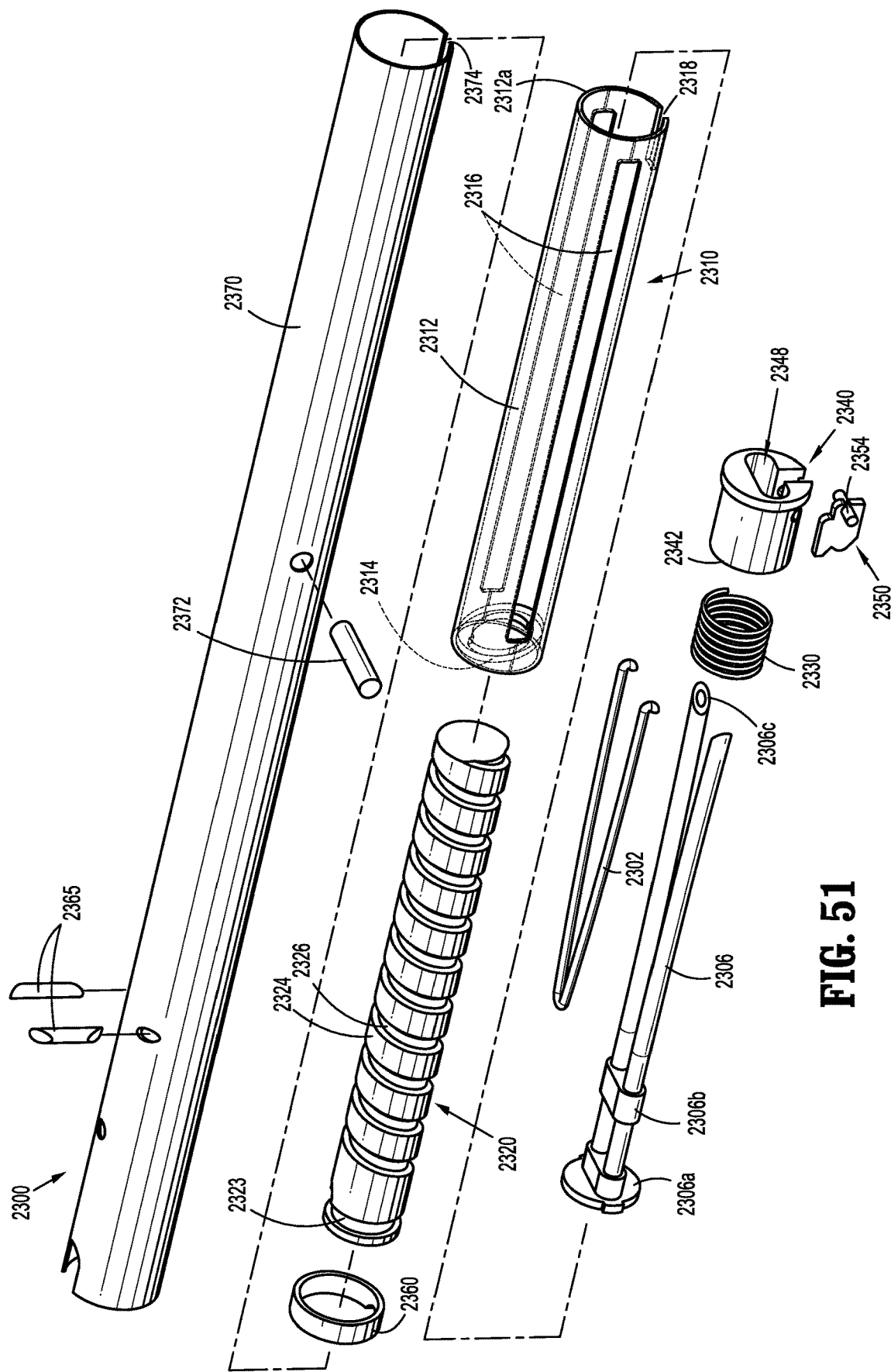
FIG. 51 is an assembly view of the end effector of FIG. 50.
Figures 52, 53:
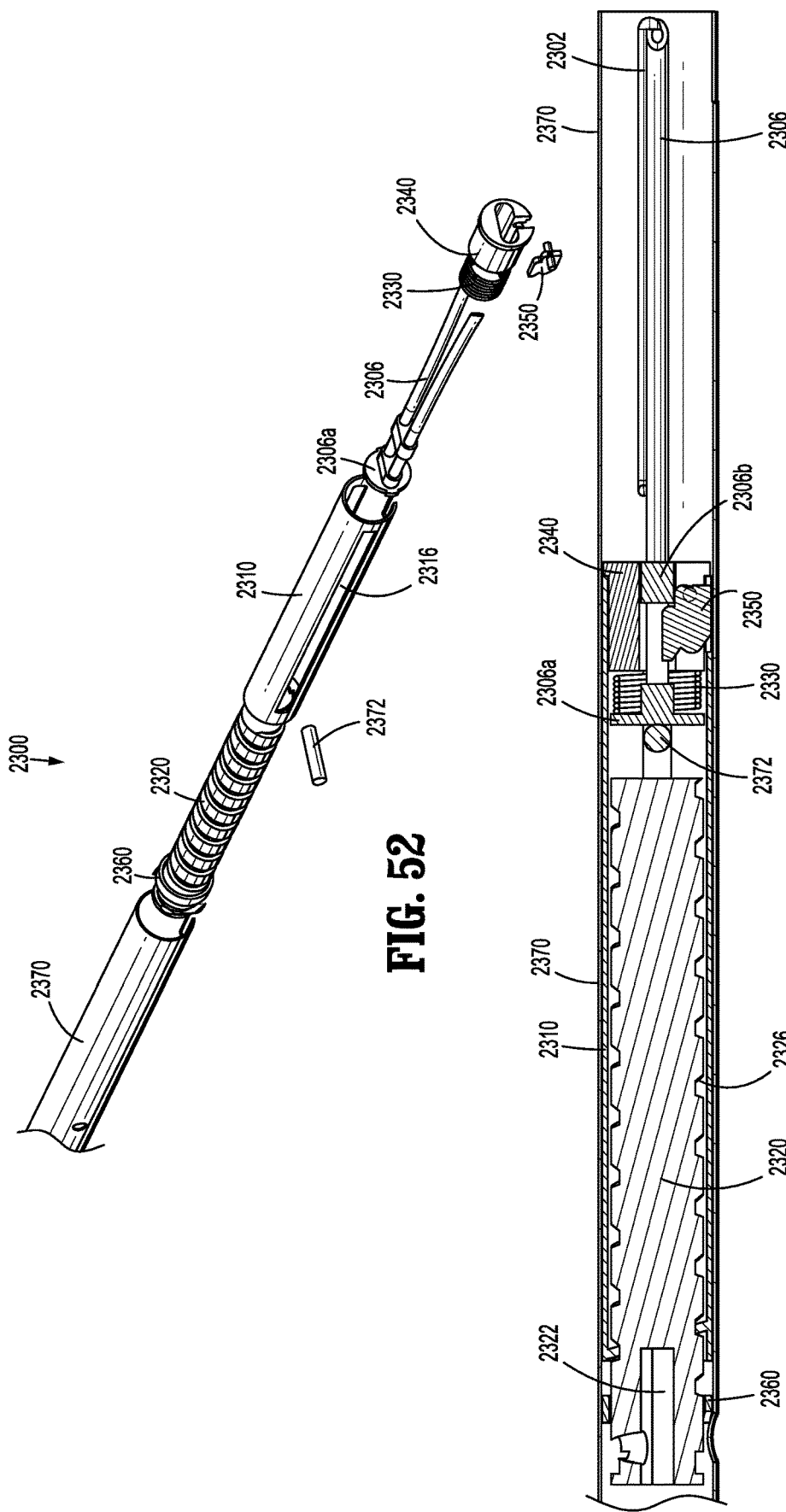
FIG. 52 is a perspective view of portions of the end effector of FIGS. 50-51 shown with parts separated.
FIG. 53 is a cross-sectional view of the end effector of FIGS. 50-52.

With particular reference to FIG. 51, end effector 2300 includes a driver 2310, a drive assembly 2320, a spring 2330, an end cap 2340, a lock 2350, a ring 2360, pins 2365, and an outer tube 2370.

Drive assembly 2320 of end effector 2300 is mechanically engaged (e.g., operatively coupled, directly affixed, etc.) to drive rod 150 of surgical device 100 of the present disclosure. Rotation of the drive rod 150 in the general direction of arrow "SLA" in FIG. 54 results in a corresponding rotation of drive assembly 2320. Drive assembly 2320 includes an aperture 2322 (FIG. 53), a proximal recess 2323, and a body portion 2324 including a helical groove 2326. Aperture 2322 of drive assembly 2320 is configured to engage the drive rod 150 of the surgical device 100. Proximal recess 2323 of drive assembly 2320 is configured to rotationally engage pins 2365, which extend through apertures of outer tube 2370 such that drive assembly 2320 is longitudinally fixed with respect to outer tube 2370. Helical groove 2326 of drive assembly 2320 is configured to rotationally engage an engagement structure 2314 of driver 2310. Additionally, ring 2360 of end effector 2300 is fixed to drive assembly 2320.

Driver 2310 of end effector 2300 includes a body portion 2312, engagement structure 2314 disposed at a proximal portion of body portion 2312, a pair of longitudinal slots 2316 extending therethrough, and a distal slot 2318. Engagement structure 2314 of driver 2310 is configured to engage helical groove 2326 of drive assembly 2320. While engagement structure 2314 is illustrated as a helical thread, engagement structure 2314 may also be a pin or the like. Due to the engagement between engagement structure 2314 and helical groove 2326 of drive assembly 2320, rotation of drive assembly 2320 results in longitudinal translation of driver 2310. Longitudinal slots 2316 of driver 2310 are configured to slidingly receive a pin 2372, such that pin 2372 helps guide longitudinal translation of driver 2310 with respect to outer tube 2370. Distal slot 2318 of driver 2310 is configured to allow a portion of lock 2350 to pass therethrough.

Biasing element or spring 2330 (e.g., a compression spring) of end effector 2300 is disposed proximally of and in contact with a proximal face 2342 of end cap 2340, and distally of and in contact with a proximal base 2306a of needle 2306. Spring 2330 is configured to bias needle 2306 proximally with respect to outer tube 2370.

Figures 54, 55:
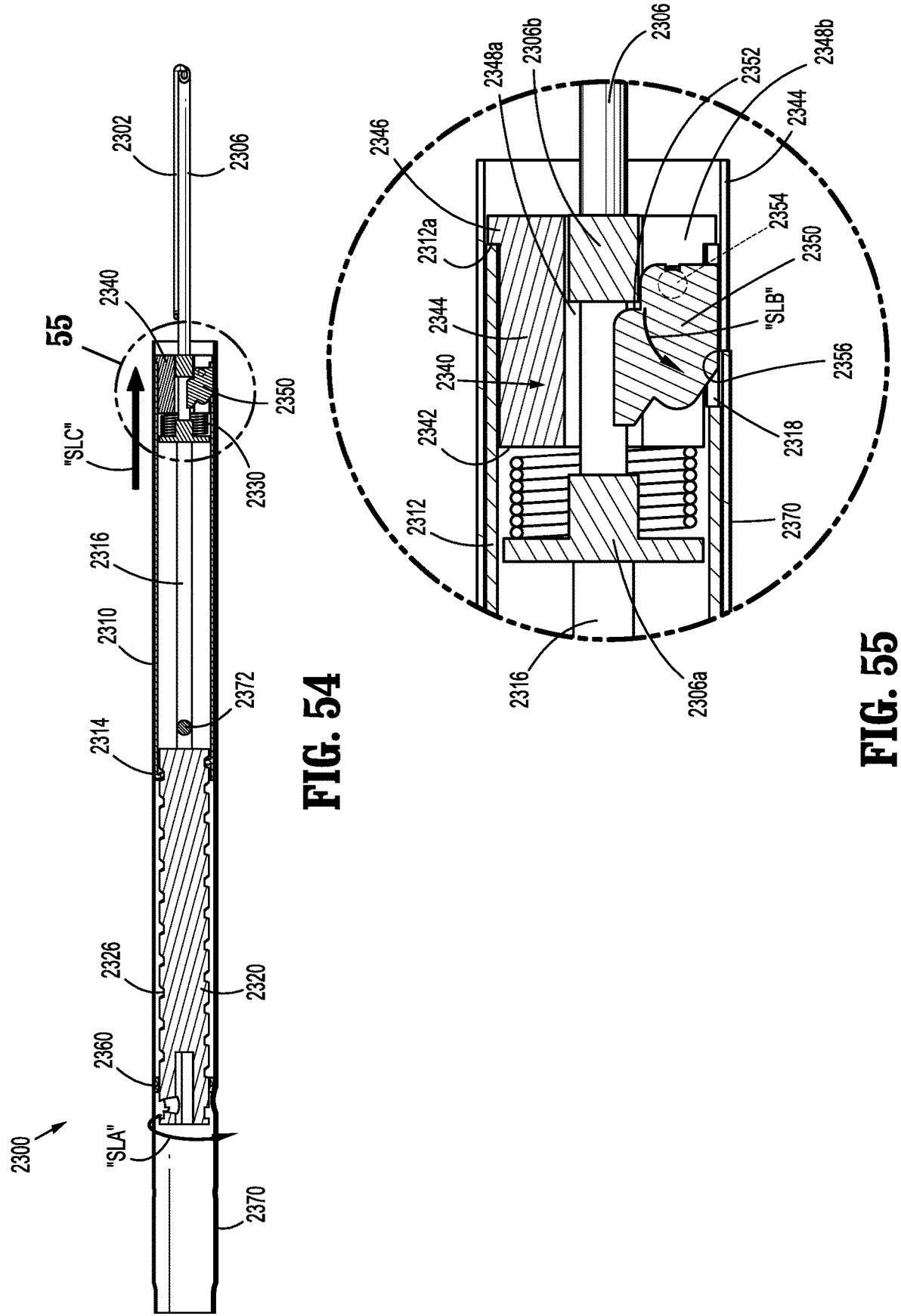
FIG. 54 is a cross-sectional view of the end effector of FIGS. 50-53 illustrating a needle in an advanced position.
FIG. 55 is an enlarged view of the area of detail indicated in FIG. 54.
Figure 58:
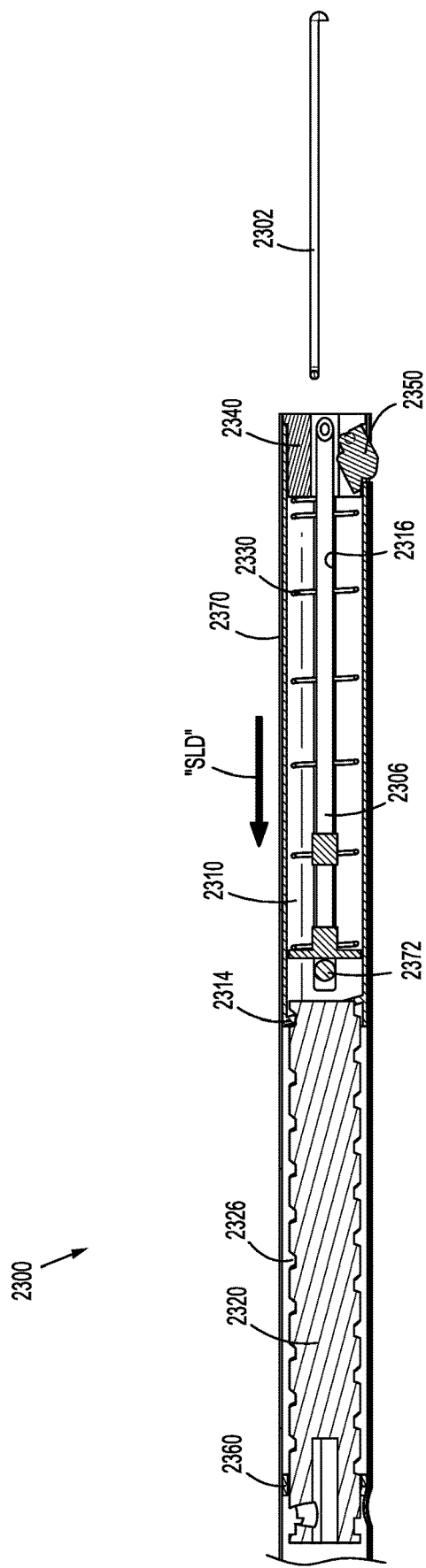
FIG. 58 is a cross-sectional view of the end effector of FIGS. 50-57 illustrating the needle in a retracted position and a suture that has been ejected from the end effector.
Figure 59:
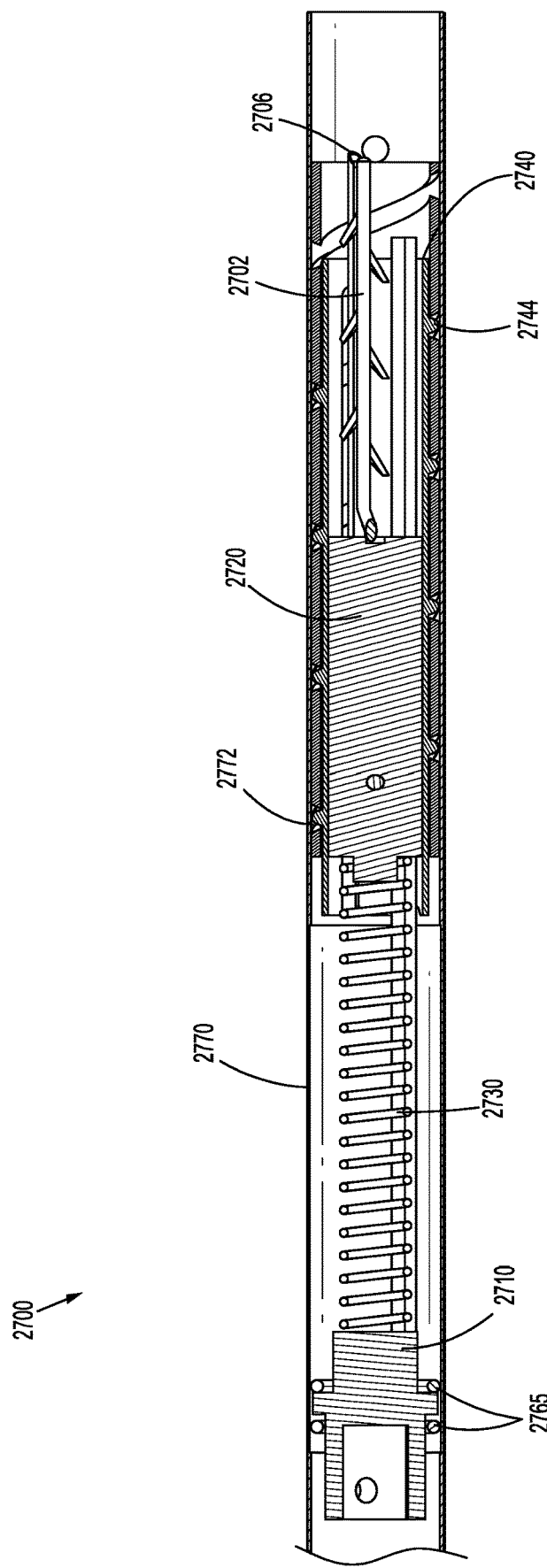
FIG. 59 is a cross-sectional view of an end effector in accordance with embodiments of the present disclosure.

End cap 2340 of end effector 2300 is disposed radially within outer tube 2370 and includes proximal face 2342, a body portion 2344, a distal lip 2346, and a groove 2348. With particular reference to FIG. 55, a distal end of driver 2310 of end effector 2300 is configured to be positioned radially outward of body portion 2344 of end cap 2340, and a distal-most edge 2312a of body portion 2312 of driver 2310 is configured to abut distal lip 2346 of end cap 2340. Groove 2348 of end cap 2340 includes a first section 2348a configured to slidingly receive a portion of needle 2306, and a second section 2348b configured to receive a portion of lock 2350.

Lock 2350 of end effector 2300 is pivotable or rotatable at least partially within second section 2348b of groove 2348 with respect to end cap 2340. Moreover, lock 2350 is pivotable between a first position (FIG. 55) where an entirety of lock 2350 is disposed radially inward of outer tube 2370, and a second position (FIG. 57) where a portion of lock 2350 extends through distal slot 2318 of driver 2310 and through a distal slot 2374 of outer tube 2370 such that a portion of lock 2350 is disposed radially outward of outer tube 2370.

In its first position, a contact portion 2352 of lock 2350 is configured to engage, abut or contact a hub 2306b of needle 2306. The proximal force exerted by spring 2330 on needle 2306 causes needle 2306 to exert a proximal force on lock 2350, which would cause lock 2350 to pivot about a lock pin 2354 in the general direction of arrow "SLB" in FIG. 55. However, the engagement between a blocking portion 2356 of lock 2350 and an inner wall of outer tube 2370 prevents lock 2350 from pivoting towards its second position. Thus, the engagement between lock 2350 and proximal hub 2306b of needle 2306 prevents spring 2330 from moving needle 2306 proximally with respect to end cap 2340.

With particular reference to FIG. 57, in response to a predetermined amount of distal travel of driver 2310 of end effector 2300 and end cap 2340 of end effector 2300, lock 2350 is able to move toward its second position. That is, after driver 2310 and end cap 2340 have been distally advanced into a position where blocking portion 2356 of lock 2350 is axially aligned with distal slot 2374 of outer tube 2370, the inner wall of outer tube 2370 no longer resists the pivoting force exerted by spring 2330 onto lock 2350. Thus, lock 2350 is able to pivot in the general direction of arrow "SLB" such that a portion of lock 2350 extends through distal slot 2374 of outer tube 2370. Here, contact portion 2352 of lock 2350 is no longer in engagement with proximal hub 2306b of needle 2306. Accordingly, the proximal force exerted by spring 2330 onto needle 2306 is no longer opposed, and needle 2306 translates proximally with respect to outer tube 2370.

Ring 2360 (e.g., an O-ring) of end effector 2300 is positioned radially outward of a proximal portion of drive assembly 2320. Ring 2360 helps maintain appropriate spacing between drive assembly 2320 and outer tube 2370, and helps facilitate rotation of drive assembly 2320 with respect to outer tube 2370.

Outer tube 2370 of end effector 2300 is configured for positioning radially outward of at least portions of suture 2302, needle 2306, driver 2310, drive assembly 2320, spring 2330, end cap 2340, lock 2350, and ring 2360.

In use, in response to at least a partial actuation of the trigger 112 of surgical device 100, the drive rod 150 rotates, as discussed above. With reference to FIGS. 54-55, initial rotation of the drive rod 150 results in a corresponding rotation of drive assembly 2320 of end effector 2300 with respect to outer tube 2370 of end effector 2300 in the general direction of arrow "SLA" in FIG. 54. Due to the engagement between helical groove 2326 of drive assembly 2320 and engagement structure 2314 of driver 2310, rotation of drive assembly 2320 in the general direction of arrow "LSA" results in distal translation of driver 2310 with respect to outer tube 2370 in the general direction of arrow "SLC" in FIG. 54. Distal translation of driver 2310 causes a corresponding distal translation of end cap 2340, lock 2350, needle 2306 and suture 2302.

Continued rotation of drive assembly 2320 in the general direction of arrow "SLA" causes continued distal advancement of driver 2310, end cap 2340, lock 2350, needle 2306 and suture 2302 until a distal tip 2306c of needle 2300 extends a sufficient distance distally beyond a distal end of outer tube 2370. Thus, to insert needle 2306 into tissue, a distal end of end effector 2300 is positioned adjacent or in contact with tissue, and the trigger of surgical device 100 is actuated (e.g., a full actuation of the trigger), thus distally advancing a portion of needle 2306 into tissue.

With particular reference to FIGS. 56 and 57, after a predetermined amount of rotation of drive assembly 2320 and distal travel of driver 2310, end cap 2340, lock 2350, needle 2306 and suture 2302 (e.g., corresponding to when distal tip 2306c is sufficiently advanced within tissue), blocking portion 2356 of lock 2350 is axially aligned with distal slot 2374 of outer tube 2370, which allows lock 2350 to pivot toward its second position (FIG. 57). In this position, lock 2350 no longer resists the proximal force exerted by spring 2330 on needle 2306, thus permitting needle 2306 to move proximally with respect to outer tube 2370 in the general direction of arrow "SLD" in FIG. 58. That is, since the proximal force exerted by spring 2330 is no longer opposed by the engagement between lock 2350 and outer tube 2370, needle 2306 is able to move proximally in the general direction of arrow "SLD" until needle 2306 reaches the approximate position shown in FIG. 58. As shown, suture 2302 remains outside of end effector 2300 (e.g., at least partially within tissue).

Stored Energy Spring

Referring now to FIGS. 59-67, an embodiment of an end effector 2700 including a pre-loaded spring assembly is shown. End effector 2700 is configured for use in connection with surgical device 100. Generally, end effector 2700 is configured to advance needles 2706 and to eject a barbed suture 2702 towards tissue. While FIGS. 59-67 illustrate a particular type of barbed suture 2702 and a particular type of needle 2706, end effector 2700 may be used with different types of sutures and/or needles.

Figure 60:
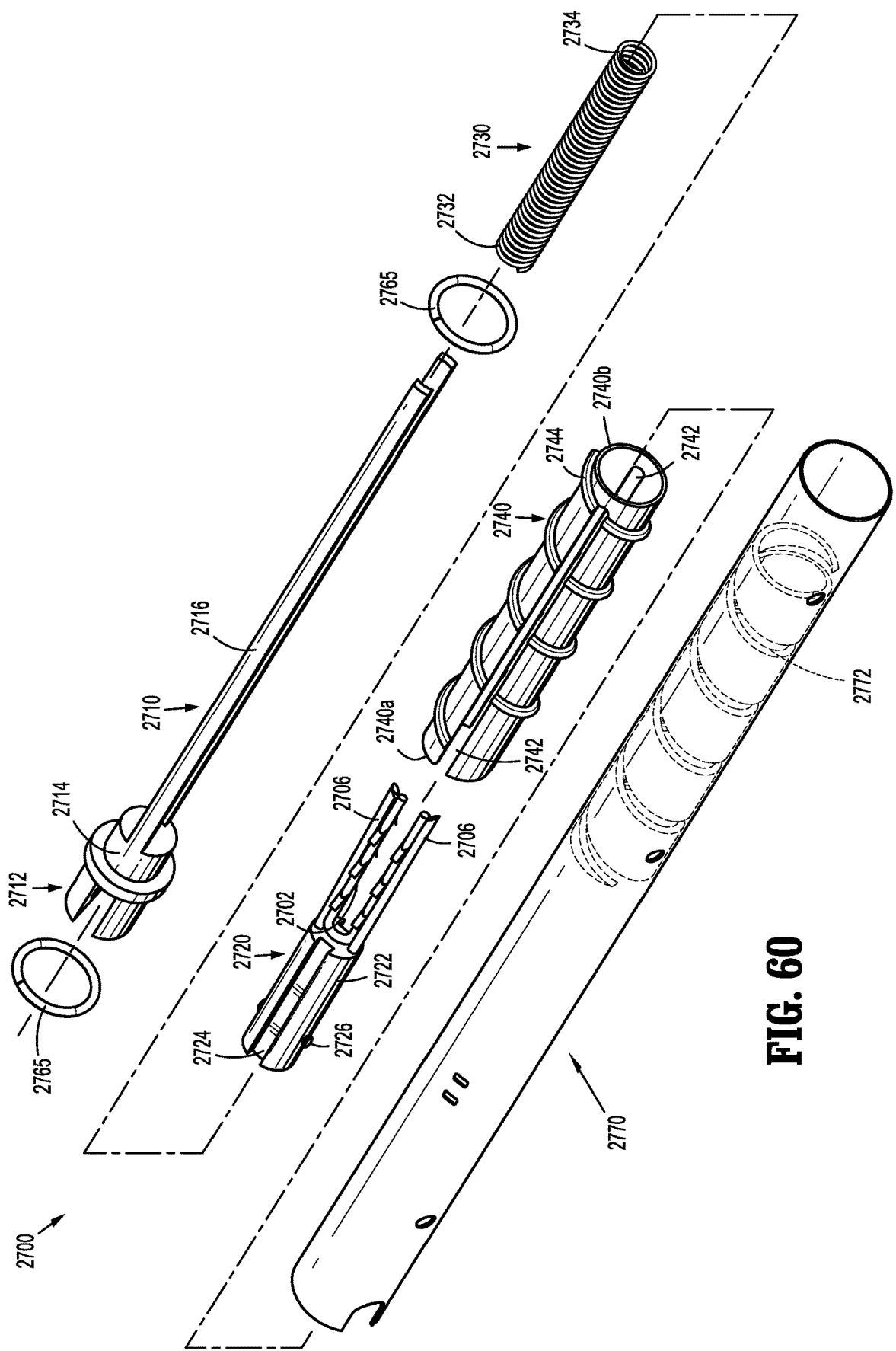
FIG. 60 is an assembly view of the end effector of FIG. 59.

With particular reference to FIG. 60, end effector 2700 includes a drive assembly 2710, a needle assembly 2720, a biasing element 2730, a helix or coil assembly 2740, a pair of rings 2765, and an outer tube 2770.

Drive assembly 2710 of end effector 2700 is mechanically engaged (e.g., operatively coupled, directly affixed, etc.) to drive rod 150 of surgical device 100 of the present disclosure. Drive assembly 2710 includes a proximal portion 2712, a body portion 2714, and a pair of arms 2716 extending distally from body portion 2714.

Needle assembly 2720 of end effector 2700 includes a body portion 2722, a pair of grooves 2724 extending longitudinally through body portion 2722, and a pin 2726 extending laterally through body portion 2722. Needles 2706 extend distally from body portion 2722 and support (e.g., frictionally support) barbed suture 2702 therebetween.

Biasing element 2730, e.g., a compression spring, of end effector 2700 includes a proximal portion 2732 and a distal portion 2734. Proximal portion 2732 of biasing element 2730 is positioned in contact with (e.g., engaged with or affixed to) a distal end of body portion 2714 of drive assembly 2710. Distal portion 2734 of biasing element 2730 is positioned in contact with (e.g., engaged with or affixed to) a proximal end of needle assembly 2720. Biasing element 2730 is configured to bias needle assembly 2720, needles 2706 and barbed suture 2702 distally with respect to outer tube 2770.

Helix or coil assembly 2740 of end effector 2700 is generally cylindrical in shape, and is hollow. Helix or coil assembly 2740 includes a pair of longitudinal slots 2742 extending from a proximal end 2740a of helix or coil assembly 2740 toward a distal end 2740b of helix or coil assembly 2740. Each longitudinal slot 2742 of helix or coil assembly 2740 is configured to slidingly engage a portion of pin 2726 extending through needle assembly 2720, such that needle assembly 2720 is longitudinally translatable with respect to helix or coil assembly 2740. Helix or coil assembly 2740 also includes a helical thread 2744 configured to rotationally engage a helical groove 2772 of outer tube 2770, such that helix or coil assembly 2740 is rotatable and longitudinally translatable with respect to outer tube 2770.

Rings 2765 (e.g., O-rings) of end effector 2700 are positioned radially outward of portions of drive assembly 2710. Rings 2765 help maintain appropriate spacing between drive assembly 2710 and outer tube 2770, and help facilitate rotation of drive assembly 2710 with respect to outer tube 2770.

Outer tube 2770 of end effector 2700 is configured for positioning radially outward of at least portions of barbed suture 2702, needles 2706, drive assembly 2710, needle assembly 2720, biasing element 2730, helix or coil assembly 2740, and pair of rings 2765. Helical groove 2772 of outer tube 2770 is configured to rotationally engage helix or coil assembly 2740, such that helix or coil assembly 2740 is rotatable and longitudinally translatable with respect to outer tube 2770.

As shown in FIG. 63, prior to use, pin 2726 of needle assembly 2720 is in contact with proximal end 2740a of helix or coil assembly 2740. This contact between pin 2726 and helix or coil assembly 2740 resists the distal bias of biasing element 2730, and thus prevents needle assembly 2720 from distally translating with respect to outer tube 2770. Additionally, in its initial position, helix or coil assembly 2740 is disposed at a distal position with respect to outer tube 2770, and helical thread 2744 of helix or coil assembly 2740 is engaged with helical groove 2772 of outer tube 2770.

In use, in response to at least a partial actuation of the trigger 112 of surgical device 100, drive rod 150 of surgical device 100 rotates, as discussed above. With reference to FIGS. 63-66, initial rotation of the drive rod 150 results in a corresponding rotation of drive assembly 2710 with respect to outer tube 2770 and with respect to helix or coil assembly 2740. Rotation of drive assembly 2710 with respect to outer tube 2770 causes a corresponding rotation of needle assembly 2720 with respect to outer tube 2770 due to the engagement between arms 2716 of drive assembly 2710 and grooves 2724 of needle assembly 2720. A predetermined amount of rotation (e.g., about 90°) of drive assembly 2770, and thus needle assembly 2720, in the general direction of arrow "SEA" (FIG. 63) causes pin 2724 of needle assembly 2720 to rotate along proximal end 2740a of helix or coil assembly 2740 until pin 2724 is aligned with longitudinal slots 2742 of helix or coil assembly 2740.

In this position, where pin 2724 is aligned with longitudinal slots 2742, pin 2724 is no longer in contact with proximal end 2740a of helix or coil assembly 2740, thus there is nothing significantly resisting the distally-directed force of biasing element 2730. Accordingly, biasing element 2730 forces needle assembly 2720 to move distally with respect to helix or coil assembly 2740, guided by the engagement between pin 2724 and longitudinal slots 2742 (see FIG. 64).

As needle assembly 2720 and needles 2706 travel distally, a distal portion of needles 2706 (e.g., distal tip 2706a) and barbed suture 2702 distally exit outer tube 2770, and engage tissue/mesh, for instance. Distal movement of needle assembly 2720 and needles 2706 with respect to outer tube 2770 continues until pin 2724 contacts distal ends 2742a (FIG. 66) of longitudinal slots 2742. Engagement between pin 2724 and distal ends 2742a of longitudinal slots 2742 resists the distal bias of biasing element 2730, thus resulting in needle assembly 2720 and needles 2706 ceasing their distal travel with respect to outer tube 2770.

Figure 65:
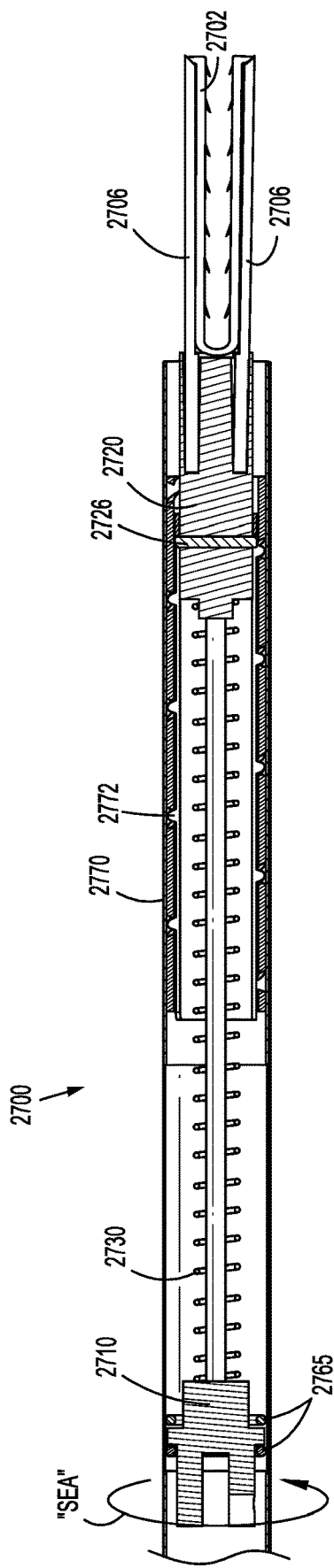
FIG. 65 is a cross-sectional view of the end effector of FIGS. 59-64 illustrating the needle assembly in an advanced position.
Figure 66:
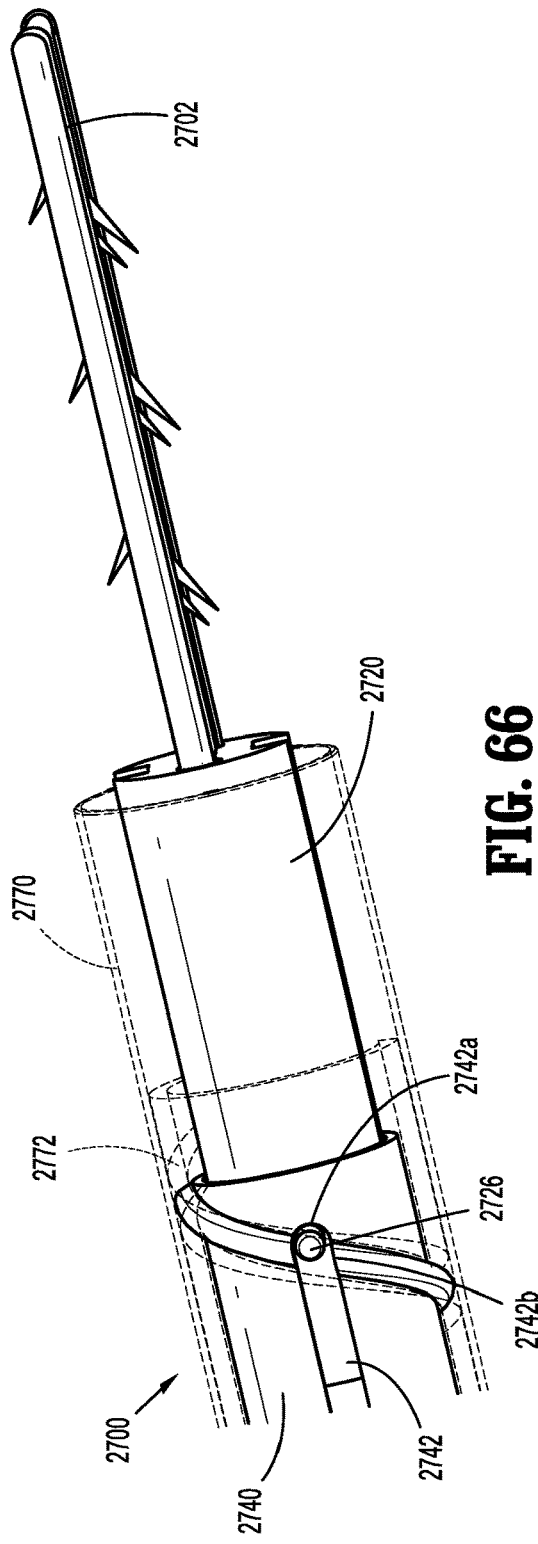
FIG. 66 is a perspective view of a distal portion of the end effector of FIGS. 59-68 illustrating the needle assembly in an advanced position.
Figure 67:
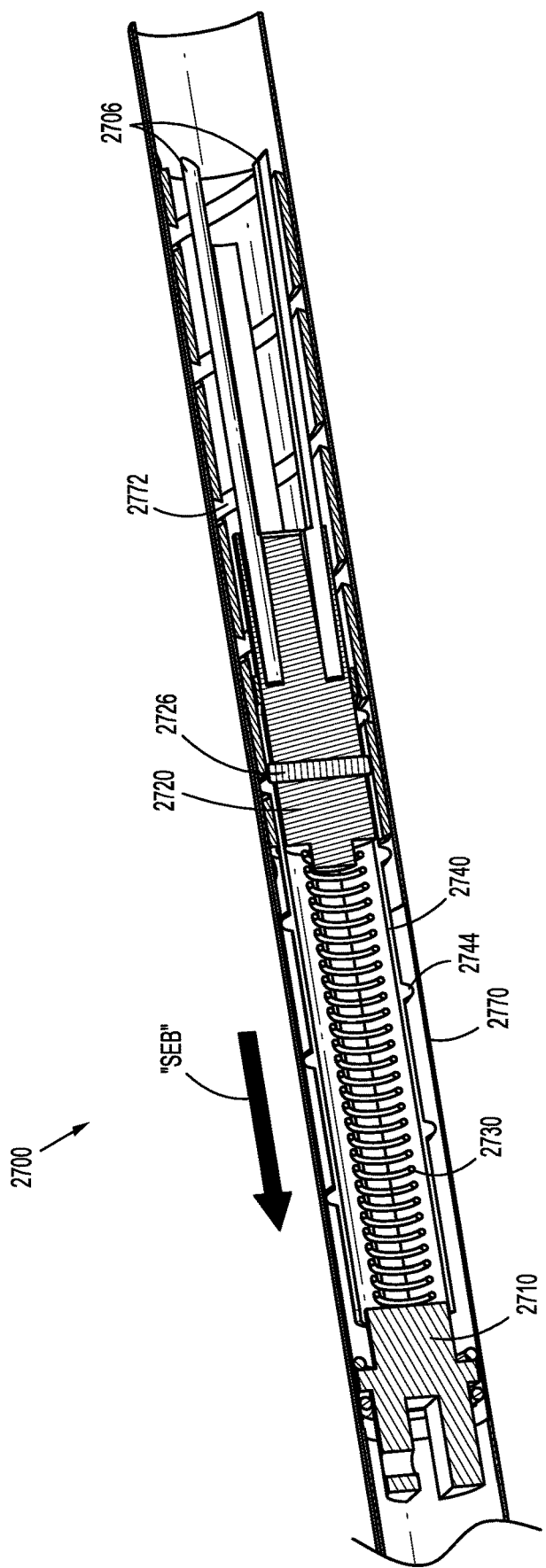
FIG. 67 is a cut-away view of the end effector of FIGS. 59-66 illustrating the needle assembly in a retracted position.

Additionally, and with reference to FIGS. 65-67, after drive assembly 2710 initially rotates (e.g., about 90°) and causes needle assembly 2720 and needles 2706 to travel distally (as discussed above), drive assembly 2710 continues to rotate (e.g., up to about 270°) in the general direction of arrow "SEA" in response to continued actuation of the trigger 112, for example. Continued rotation of drive assembly 2710 causes a corresponding rotation of needle assembly 2720 and pin 2724 with respect to outer tube 2770. Rotation of needle assembly 2720 now causes a corresponding rotation of helix or coil assembly 2740 due to the engagement between needle 2724 and a sidewall 2742b of longitudinal slot 2742.

Moreover, when helix or coil assembly 2740 rotates with respect to outer tube 2770, the engagement between helical thread 2744 of helix or coil assembly 2740 and helical groove 2772 of outer tube 2770 causes helix or coil assembly 2740 to move proximally with respect to outer tube 2770 in the general direction of arrow "SEB" in FIG. 67. Due to the engagement between distal ends 2742a of longitudinal slots 2742 of helix or coil assembly 2740 and pin 2724 of needle assembly 2720, proximal movement of helix or coil assembly 2740 also causes a corresponding proximal movement of needle assembly 2720. Needle assembly 2720 and needles 2706 are movable proximally until distal tips 2706a of needles 2706 are longitudinally aligned with or proximal of a distal end of outer tube 2770, thereby reducing the possibility of a user unintentionally contacting needles 2706.

While some embodiments of end effectors described herein have been described as being re-usable, it is contemplated that any of the end effectors described herein are configured for release, reloading and/or reuse.

In accordance with the present disclosure, it is contemplated that an electromechanical control module may replace handle assembly 110 to actuate the surgical device 100. The electromechanical control module may include at least one microprocessor, at least one drive motor controllable by the at least one microprocessor, and a source of power for energizing the at least one microprocessor and the at least one drive motor.

As can be appreciated, securement of any of the components of the presently disclosed devices can be effectuated using known fastening techniques such welding, crimping, gluing, etc.

Additionally, the present disclosure includes methods of using the disclosed end effectors, and methods of performing a surgical procedure utilizing the disclosed end effectors. An example of a disclosed method includes using a disclosed end effector to advance stay-sutures (e.g., four stay-sutures) through an implant (e.g., mesh) to hold the implant in a desired position, removing the end effector from the handle portion of a surgical instrument, engaging a second end effector with the same handle portion of the surgical instrument used to advance stay-sutures through the implant, and advancing tacks from the second end effector through the implant.

The present disclosure also includes surgical systems. A disclosed surgical system includes a surgical device, a first end effector and a second end effector. The surgical device includes a handle assembly and an elongated portion extending distally from the handle assembly. The first end effector is configured to releasably engage a distal portion of the elongated portion, and includes a drive assembly and a needle assembly. The drive assembly is configured to advance and retract the needle assembly upon at least a partial actuation of the handle assembly of the surgical device. The second end effector is configured to releasably engage the distal portion of the elongated portion, includes a plurality of tacks therein, and is configured to distally advance the plurality of tacks upon at least a partial actuation of the handle assembly of the surgical device.

The present disclosure also includes surgical kits including a plurality of first end effectors (e.g., pre-loaded with stay-sutures, barbed sutures, etc.), a plurality of second end effectors (e.g., pre-loaded with a plurality of tacks), and a surgical device. The surgical device includes a handle assembly and an elongated portion extending distally from the handle assembly. Each of the first end effectors and second end effectors is configured to releasably engage a distal portion of the elongated portion of the surgical device.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An end effector for use with a surgical device, the end effector comprising:
   a drive assembly;
   a driver disposed in mechanical cooperation with the drive assembly, wherein rotation of the drive assembly in a first direction causes distal translation of the driver with respect to the drive assembly;
   a needle assembly disposed in mechanical cooperation with the driver, wherein distal translation of the driver causes a corresponding distal translation of the needle assembly;
   a biasing element disposed in mechanical cooperation with the needle assembly, the biasing element configured to bias the needle assembly proximally; and
   a lock pivotably engaged with a portion of an end cap, the lock configured to help prevent the needle assembly from moving proximally with respect to the driver until the needle assembly has reached a predetermined longitudinal position.

2. The end effector according to claim 1, wherein the biasing element includes a compression spring.

3. The end effector according to claim 1, wherein the biasing element is disposed distally of a proximal base of the needle assembly.

4. The end effector according to claim 1, wherein the end cap is disposed adjacent a distal portion of the driver, the end cap being distally translatable with respect to the drive assembly.

5. The end effector according to claim 1, wherein the lock is movable from a first position where a portion of the lock engages a portion of the needle assembly to a second position where the lock is free from engagement with the needle assembly.

6. The end effector according to claim 5, wherein when the lock is in the first position, the lock resists a bias against the needle assembly provided by the biasing element.

7. The end effector according to claim 6, wherein when the lock is in the second position, the needle assembly is movable in a proximal direction with respect to the driver.

8. The end effector according to claim 5, further comprising an outer tube disposed radially outward of the driver, wherein engagement between a portion of the lock and an inner wall of the outer tube prevents the lock from moving toward the second position.

9. The end effector according to claim 1, wherein the driver includes a distal slot configured to allow a portion of the lock to pass therethrough.

10. The end effector according to claim 1, wherein the drive assembly includes a helical groove configured to engage a portion of the driver.

11. The end effector according to claim 1, further comprising an outer tube disposed radially outward of the driver, wherein the drive assembly is fixed from longitudinal movement with respect to the outer tube.

12. The end effector according to claim 1, wherein the needle assembly includes a first needle extending distally from a needle block, and second needle extending distally from the needle block, the first needle being parallel to the second needle.

13. The end effector according to claim 1, further comprising a suture disposed in mechanical cooperation with a needle of the needle assembly.

14. An end effector for use with a surgical device, the end effector comprising:
  a drive assembly;
  a driver disposed in mechanical cooperation with the drive assembly, wherein rotation of the drive assembly in a first direction causes distal translation of the driver with respect to the drive assembly;
  a needle assembly disposed in mechanical cooperation with the driver, wherein distal translation of the driver causes a corresponding distal translation of the needle assembly;
  a biasing element disposed in mechanical cooperation with the needle assembly, the biasing element configured to bias the needle assembly proximally; and
  a lock disposed in mechanical cooperation with a portion of an end cap, the lock configured to help prevent the needle assembly from moving proximally with respect to the driver until the needle assembly has reached a predetermined longitudinal position, the lock being movable from a first position where the portion of the lock engages a portion of the needle assembly to a second position where the lock is free from engagement with the needle assembly, wherein when the lock is in the first position, the lock resists a bias against the needle assembly provided by the biasing element.

15. An end effector for use with a surgical device, the end effector comprising:
  a drive assembly;
  a driver disposed in mechanical cooperation with the drive assembly, wherein rotation of the drive assembly in a first direction causes distal translation of the driver with respect to the drive assembly;
  a needle assembly disposed in mechanical cooperation with the driver, wherein distal translation of the driver causes a corresponding distal translation of the needle assembly;
  a biasing element disposed in mechanical cooperation with the needle assembly, the biasing element configured to bias the needle assembly proximally;
  a lock disposed in mechanical cooperation with a portion of an end cap, the lock configured to help prevent the needle assembly from moving proximally with respect to the driver until the needle assembly has reached a predetermined longitudinal position, the lock being movable from a first position where the portion of the lock engages a portion of the needle assembly to a second position where the lock is free from engagement with the needle assembly; and an outer tube disposed radially outward of the driver, wherein engagement between a portion of the lock and an inner wall of the outer tube prevents the lock from moving toward the second position.

16. An end effector for use with a surgical device, the end effector comprising:
  a drive assembly;
  a driver disposed in mechanical cooperation with the drive assembly, wherein rotation of the drive assembly in a first direction causes distal translation of the driver with respect to the drive assembly;
  a needle assembly disposed in mechanical cooperation with the driver, wherein distal translation of the driver causes a corresponding distal translation of the needle assembly;
  a biasing element disposed in mechanical cooperation with the needle assembly, the biasing element configured to bias the needle assembly proximally; and
  a lock disposed in mechanical cooperation with a portion of an end cap, the lock configured to help prevent the needle assembly from moving proximally with respect to the driver until the needle assembly has reached a predetermined longitudinal position, wherein the driver includes a distal slot configured to allow the portion of the lock to pass therethrough.

* * * * *